(12) United States Patent
Salaski et al.

(10) Patent No.: US 6,716,862 B2
(45) Date of Patent: Apr. 6, 2004

(54) 5-(SUBSTITUTED)-5-(SUBSTITUTEDSULFONYL OR SULFANYL) THIAZOLIDINE-2,4-DIONES USEFUL FOR INHIBITION OF FARNESYL-PROTEIN TRANSFERASE

(75) Inventors: Edward James Salaski, Tenafly, NJ (US); Semiramis Ayral-Kaloustian, Tarrytown, NY (US); Joseph William Epstein, Monroe, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 50 days.

(21) Appl. No.: 10/226,880

(22) Filed: Aug. 23, 2002

(65) Prior Publication Data

US 2003/0096849 A1 May 22, 2003

Related U.S. Application Data

(60) Provisional application No. 60/314,584, filed on Aug. 24, 2001.

(51) Int. Cl.[7] ..................... C07D 277/36; A61K 31/426
(52) U.S. Cl. ......................................... 514/369; 548/183
(58) Field of Search ........................... 514/369; 548/183

(56) References Cited

U.S. PATENT DOCUMENTS

| 5,574,051 A | 11/1996 | Wrobel et al. |
| 5,605,918 A | 2/1997 | Wrobel et al. |

FOREIGN PATENT DOCUMENTS

| WO | WO 99/05117 | 2/1999 |
| WO | WO 01/02377 | 1/2001 |
| WO | WO 01/57006 A1 | 8/2001 |
| WO | WO 01/85685 A1 | 11/2001 |

OTHER PUBLICATIONS

L.M. Harwood, M. Julia, G. Le Thuillier, *Tetrahedron*, 1980, 36, 2483–2487.
S. Nahm, S.M. Weinreb, *Tetrahedron Lett.*, 1981, 22, 3815–3818.
J.L. Bos, *Cancer Res.*, 1989, 49, 4682.
P.J. Casey, P.A. Solski, C.J. Der, J.E. Buss, *Proc. Natl. Acad. Sci. U.S.A.*, 1989, 86, 8323.
L.V. Rubinstein, R.H. Shoemaker, K.D. Paull, R.M. Simon, S. Tosini, P. Skehan, D.A. Scudiero, A. Monks, M.R. Boyd, *J. Natl. Cancer Instit.*, 1990, 82(13), 1113–1118.
P. Skehan, R. Storeng, D. Scudiero, A. Monks, J. McMohan, D. Vistica, J. Warren, J. Bokesh, S. Kenney, M.R. Boyd, *J. Natl. Cancer Instit.*, 1990, 82(13), 1107–1112.
A. Zask, I. Kirkovsky, J.W. Nowicki, M.L. McCaleb, *J. Med. Chem.*, 1990, 33, 1418–1423.
J.F. Hancock, H. Paterson, C.J. Marshall, *Cell*, 1990, 63, 133.
A. Monks, et al., *J. Natl. Cancer Instit.*, 1991, 83, 757–766.
J.F. Moomaw, P.J. Casey, *J. Biol. Chem.*, 1992, 267, 17438–17443.
M.A. Garcia, et al., *J. Biol. Chem.*, 1993, 268, 18415–18420.
G.L. Bolton, J.S. Sebolt–Leopold, J.C. Hodges; *Annu. Rep. Med. Chem.*, 1994, 29, 165.
R.J.A. Grand in "New Molecular Targets in Cancer Chemotherapy", J.D. Kerr and P. Workman, Eds. *CRC Press*, Boca Raton, FL., 1994, p. 97.
W.R. Schoen, J.M. Pisano, K. Prendergast, M.J. Wyvratt, Jr., M.H. Fisher, K. Cheng, W.S. Chan, B. Butler, R.G. Smith, R.G. Ball, *J. Med. Chem.*, 1994, 37, 897–906.
G.L. James, M.S. Brown, J.L. Goldstein, *Methods in Enzymology*, 1995, 255, 38–46.
M.R. Boyd, K.D. Paull, *Drug Development Res.*, 1995, 34, 91–109.
S.P. Fricker, R.G. Buckley, *Anticancer Research*, 1996, 16, 3755–3760.
S. Ayral–Kaloustian, J.S. Skotnicki, *Annu. Rep. Med. Chem.*, 1996, 31, 171.
H.W. Park, S.R. Boduluri, J.F. Moomaw, P.J. Casey, L.S. Beese, *Science*, 1997, 275, 1800.
T.M. Williams, *Exp. Opin. Ther. Patents*, 1998, 8, 553.
SCH–66336, *Pharmaprojects*, 1998, No. 5128.
R–115777, *Pharmaprojects*, 1998, No. 5532.
J. Wrobel, L. Zenan, A. Dietrich, M. McCaleb, B. Mihan, J. Stredy, D. Sullivan, *J. Med. Chem.*, 1998, 41, 1084–1091.
PCT International Search Report Mailed Nov. 19, 2002.

*Primary Examiner*—Robert Gerstl
(74) *Attorney, Agent, or Firm*—Daniel B. Moran

(57) ABSTRACT

The invention relates to compounds of Formula (I) wherein $R_1$, $(R_2)_v$, $R_3$ and n are defined in the specification and pharmaceutical compositions thereof, that inhibit the Ras farnesyl-protein transferase enzyme (FPTase), and may be used as an alternative to, or in conjunction with, traditional cancer therapy for the treatment of ras oncogene-dependent tumors, such as cancers of the pancreas, colon, bladder, and thyroid.

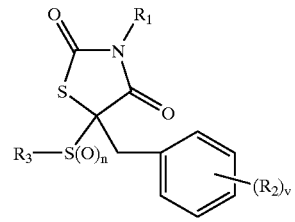

25 Claims, No Drawings

5-(SUBSTITUTED)-5-(SUBSTITUTEDSULFONYL OR SULFANYL) THIAZOLIDINE-2,4-DIONES USEFUL FOR INHIBITION OF FARNESYL-PROTEIN TRANSFERASE

This application claims priority from copending provisional application Ser. No. 60/314,584 filed on Aug. 24, 2001 the entire disclosure of which is hereby incorporated by reference.

FIELD OF THE INVENTION

The present invention relates to a novel series of 5-(substituted)-5-(substitutedsulfonyl or sulfanyl) thiazolidine-2,4-diones, to pharmaceutical compositions containing them, to their use in cancer therapy and to a process for their preparation. The compounds inhibit Ras FPTase, and may be used as an alternative to, or in conjunction with, traditional cancer therapy for treating ras oncogene-dependent tumors, such as cancers of the pancreas, colon, bladder, and thyroid. Compounds in the invention may also be useful for controlling metastasis, suppressing angiogenesis, inducing apoptosis, and in treating Ras-associated proliferative diseases other than cancer, such as restenosis, neuro-fibromatosis, endometriosis, and psoriasis. These compounds may also inhibit prenylation of proteins other than Ras, and thus be effective in the treatment of diseases associated with other prenyl modifications of proteins.

BACKGROUND OF THE INVENTION

Mammalian H-, K-, and N-Ras proteins, encoded by H-, K-, and N-ras proto-oncogenes, respectively, are 21 kD GTP-binding proteins which possess intrinsic GTPase activity and play a fundamental role in cell proliferation and differentiation (G. L. Bolton, J. S. Sebolt-Leopold, and J. C. Hodges, *Annu. Rep. Med. Chem.*, 1994, 29, 165; R. J. A. Grand in "New Molecular Targets in Cancer Chemotherapy" J. D. Kerr, and P. Workman, Eds., CRC Press, Boca Raton, Fla., 1994, p. 97). Specific mutations in the ras gene impair GTPase activity of Ras, leading to uninterrupted growth signals and to the transformation of normal cells into malignant phenotypes. Mutant ras oncogenes are found in approximately 25% of all human cancers, including 90% of pancreatic, 50% of colon, and 50% of thyroid tumors (J. L. Bos, *Cancer Res.*, 1989, 49, 4682). It has been shown that normal cells transfected with mutant ras gene become cancerous and that unfarnesylated, cytosolic mutant Ras protein does not anchor in cell membranes and cannot induce this transformation (J. F. Hancock, H. Paterson, and C. J. Marshall, *Cell*, 1990, 63, 133). Posttranslational modification and plasma membrane association of mutant Ras is essential for this transforming activity. The first and required step in the processing of Ras is farnesylation at the cysteine residue of its carboxyl terminal motif, CAAX (C=Cys-186, A=aliphatic amino acid, X=usually methionine, serine or glutamine). Since its identification, the enzyme farnesyl-protein transferase (FPTase) that catalyzes this first processing step has emerged as a promising target for therapeutic intervention (H.-W. Park, S. R. Boduluri, J. F. Moomaw, P. J. Casey, and L. S. Beese, *Science*, 1997, 275,1800; P. J. Casey, P. A. Solski, C. J. Der, and J. E. Buss, *Proc. Natl. Acad. Sci. U.S.A.*, 1989, 86, 8323; S. Ayral-Kaloustian and J. S. Skotnicki, *Annu. Rep. Med. Chem.*, 1996, 31,165, and references therein). Major milestones have been achieved with small molecules, such as mimics of the tetrapeptide CAAX and analogs of farnesyl pyrophosphate, that show efficacy without toxicity in vitro as well as in mouse models bearing ras-dependent tumors or human xenografts with H-, N-, or K-ras mutations (S. Ayral-Kaloustian and J. S. Skotniciki, *Annu. Rep. Med. Chem.*, 1996, 31, 165, and references therein; T. M. Williams, *Exp. Opin. Ther. Patents*, 1998, 8, 553, and references therein). Several low-molecular weight compounds that inhibit FPTase have entered Phase I trials in humans (SCH-66336, *Pharmaprojects*, 1998, No. 5128; R-115777, *Pharmaprojects*, 1998, No. 5532).

5-[3-aryl-prop-2-ynyl]-5-(arylsulfonyl)thiazolidine-2,4-diones and 5-[3-aryl-prop-2-ynyl]-5-(arylsulfanyl) thiazolidine-2,4-diones which possess antihyperglycemic activity, are reported in U.S. Pat. Nos. 5,574,051 and 5,605,918.

Accordingly, there is still a need for drugs for treating and preventing cancer. In particular, there is a need for drugs which inhibit or treat the growth of tumors expressing an activated Ras oncogene and which include cancers of the pancreas, colon, bladder and thyroid.

The present invention further provides a method of treatment of ras oncogene-dependent tumors, such as cancers of the pancreas, colon, bladder, and thyroid; a method of controlling metastasis, suppressing angiogenesis, and inducing apoptosis; a method of treating Ras-associated proliferative diseases other than cancer, such as restenosis, neuro-fibromatosis, endometriosis, and psoriasis. The compounds of the present invention may also inhibit prenylation of proteins other than Ras, and thus provide a method of treatment of diseases associated with other prenyl modifications of proteins.

SUMMARY OF THE INVENTION

The present invention discloses compounds represented by Formula (I):

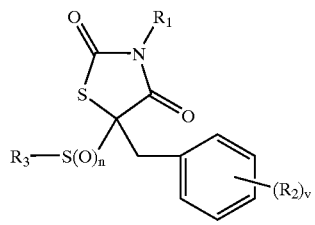

Formula (I)

wherein:

$R_1$ is hydrogen, $-CH_2-CO_2R_9$, or $-CH_2-C(O)NHOR_{10}$;

n is an integer of 0 or 2;

v is an integer of 1 to 3;

each $R_2$ is independently hydrogen, alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkyl(1 to 12 carbon atoms)amino, di(alkyl of 1 to 12 carbon atoms)amino, monoaryl(6 to 12 carbon atoms)amino, alkyl(1 to 12 carbon atoms)aryl(6 to 12 carbon atoms)amino, di(aryl of 6 to 12 carbon atoms) amino, monocycloalkyl(3 to 7 carbon atoms)amino, di(cycloalkyl of 3 to 7 carbon atoms)amino, alkyl(1 to 12 carbon atoms)cycloalkyl(3 to 7 carbon atoms) amino, aryl(6 to 12 carbon atoms)cycloalkyl(3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl(1 to 12 carbon atoms), carboxyaryl(6 to 12 carbon atoms), carboxycycloalkyl(3 to 7 carbon atoms), formyl, acyloxy of 1 to 12 carbon atoms, cyano, alkyl(1 to 12 carbon atoms)carbonyldioxy, aryl(6 to 12 carbon atoms)carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, monoalkyl(1 to 12 carbon atoms)carbamyl, di(alkyl of 1 to 12 carbon atoms) carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aminocarbonyloxy, aminocarbonylamino, or optionally when v is an integer of 1, the moiety

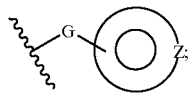

wherein the moiety

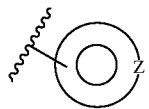

is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

heteroaryl of 5 to 12 ring atoms optionally-substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy and a moiety of the formula:

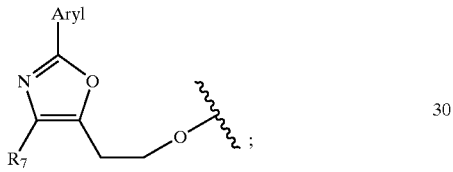

G is a single covalent bond, $-O-$, $-S-$, $-SO-$, $-SO_2-$, $-N-R_4$, $-CH_2-$, $-CHOR_4$, $-CR_8OR_4$, $-C(OR_5)_2$, $-CO-$, $-CS-$, $-C=N-R_6$ or moieties of the formulae:

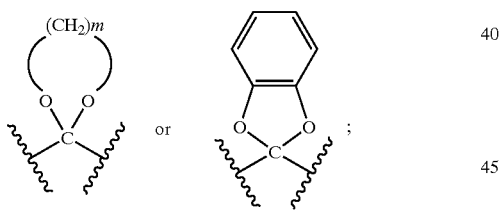

m is an integer of 2 to 4;

$R_3$ is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

or heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_4$ is hydrogen, alkyl of 1 to 12 carbon atoms, cycloalkyl of 3 to 7 carbon atoms, aryl of 6 to 12 carbon atoms optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

acyl of 1 to 12 carbon atoms, carboxyalkyl of 1 to 12 carbon atoms, carboxycycloalkyl of 3 to 7 carbon atoms, carboxyaryl of 6 to 12 carbon atoms wherein the aryl is optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms; formyl, carbamyl, monoalkyl(1 to 12 carbon atoms)carbamyl, di(alkyl of 1 to 12 carbon atoms)carbamyl, monoaryl(6 to 12 carbon atoms) carbamyl, di(aryl 6 to 12 carbon atoms)carbamyl, monocycloalkyl(3 to 7 carbon atoms)carbamyl, di(cycloalkyl 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, monoalkyl(1 to 12 carbon atoms)carboxyl, di(alkyl of 1 to 12 carbon atoms) carboxyl, monoaryl(6 to 12 carbon atoms)carboxyl, di(aryl 6 to 12 carbon atoms)carboxyl, monocycloalkyl(3 to 7 carbon atoms)carboxyl, di(cycloalkyl 3 to 7 carbon atoms)carboxyl, aryl(6 to 12 carbon atoms)alkyl(1 to 12 carbon atoms)carboxyl, cycloalkyl(3 to 7 carbon atoms)alkyl(1 to 12 carbon atoms)carboxyl, cycloalkyl(3 to 7 carbon atoms)aryl(6 to 12 carbon atoms) carboxylperfluoroaryl, monoalkyl(1 to 12 carbon atoms)thiocarbamyl, di(alkyl of 1 to 12 carbon atoms)thiocarbamyl, monoaryl(6 to 12 carbon atoms)thiocarbamyl, di(aryl 6 to 12 carbon atoms)thiocarbamyl, monocycloalkyl(3 to 7 carbon atoms)thiocarbamyl, di(cycloalkyl 3 to 7 carbon atoms) thiocarbamyl, aryl(6 to 12 carbon atoms)alkyl(1 to 12 carbon atoms)thiocarbamyl, cycloalkyl(3 to 7 carbon atoms)alkyl(1 to 12 carbon atoms) thiocarbamyl, or cycloalkyl(3 to 7 carbon atoms)aryl(6 to 12 carbon atoms)thiocarbamyl; heteroaryl of 5 to 12 ring atoms optionally substituted with 1 to 3 groups independently selected alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms) (cycloalkyl of 3 to 7 carbon atoms)amino, (aryl of 6 to 12 carbon atoms)(cycloalkyl of 3 to 7 carbon atoms) amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_5$ is alkyl of 1 to 12 carbon atoms;

$R_6$ is alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, di(alkyl of 1 to 12 carbon atoms)amino, monoarylamino of 6 to 12 carbon atoms, alkyl(of 1 to 12 carbon atoms)aryl(of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, alkyl(of 1 to 12 carbon atoms)cycloalkyl (of 3 to 7 carbon atoms)amino, aryl(of 6 to 12 carbon atoms)cycloalkyl(of 3 to 7 carbon atoms)amino, arylsulfamoyl of 6 to 12 carbon atoms;

$R_7$ is alkyl of 1 to 12 carbon atoms;

$R_8$ is alkyl of 1 to 12 carbon atoms, cycloalkyl of 3 to 7 atoms and phenyl;

$R_9$ is hydrogen or alkyl of 1 to 6 carbon atoms;

$R_{10}$ is hydrogen or benzyl optionally substituted with nitro; and the pharmacologically acceptable salts thereof.

Among the preferred compounds of Formula (I) of this invention are those in the subgroups, and pharmaceutically acceptable salts thereof:

a. $R_3$ is aryl; $R_1$ is H; and v is an integer of 1;

b. $R_3$ is aryl; $R_1$ is H; v is an integer of 1 and $R_2$ is a moiety

d. $R_3$ is aryl; v is an integer of 1; $R_2$ is the moiety

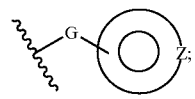

the moiety

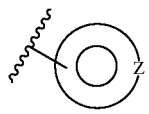

is heteroaryl optionally substituted with 1 to 3 groups independently selected.

e. $R_3$ is aryl; v is an integer of 1; $R_2$ is the moiety

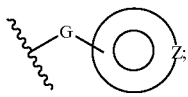

the moiety

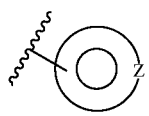

is aryl optionally substituted with 1 to 3 groups independently selected.

Among the most particularly preferred compounds of this invention according to general Formula (I) are the following compounds or pharmaceutically acceptable salts thereof for treating or controlling ras oncogene-dependent tumors and associated proliferative diseases in warm-blooded animals preferably mammals, most preferably humans in need thereof are the following compounds or a pharmaceutically acceptable salt thereof:

5-(4-[2-(5-Methyl-2-phenyloxazol-4-yl)ethoxy]benzyl)-5-(4-methylbenzenesulfonyl)thiazolidine-2,4-dione, 5-(4-Bromo-2-fluorobenzyl)-5-(4-methylbenzenesulfonyl)thiazolidine-2,4-dione, 5-(3,4-Dichlorobenzyl)-5-(4-methylbenzenesulfonyl)thiazolidine-2,4-dione, 5-(4-Bromo-2-fluorobenzyl)-5-(naphthalene-2-sulfonyl)thiazolidine-2,4-dione, 5-(4-[2-(5-Methyl-2-phenyloxazol-4-yl)ethoxy]benzyl)-5-(naphthalene-2-sulfonyl)thiazolidine-2,4-dione, 5-Benzyl-5-(4-methoxybenzenesulfonyl)thiazolidine-2,4-dione, 2-[5-Benzyl-5-(4-methoxybenzenesulfonyl)-2,4-dioxothiazolidin-3-yl]-N-hydroxyacetamide, 5-(3-[2-(4-Methoxyphenyl)[1,3]dioxolan-2-yl]benzyl)-5-(4-methylbenzenesulfanyl)thiazolidine-2,4-dione, 5-(3-[2-(4-Methoxyphenyl)[1,3]dioxolan-2-yl]benzyl)-5-(4-methylbenzenesulfonyl)thiazolidine-2,4-dione, 5-(3-(4-methoxybenzoyl)benzyl)-5-(4-methylbenzenesulfonyl)thiazolidine-2,4-dione, 5-(3-(4-methoxybenzoyl)benzyl)-5-(4-methylbenzenesulfanyl)thiazolidine-2,4-dione, 5-(3-[Hydroxy(4-methoxyphenyl)methyl]-benzyl)-5-(4-methylbenzenesulfanyl)thiazolidine-2,4-dione, 5-(4-Bromobenzyl-5-(4-methylbenzenesulfonyl)thiazolidine-2,4-dione, 5-[2'-cyanobiphen-4-ylmethyl]-5-(4-methylbenzenesulfonyl)thiazolidine-2,4-dione, 5-[2'-(1H-Tetrazol-5-yl)biphen-4-ylmethyl]-5-(4-methylbenzenesulfonyl)thiazolidine-2,4-dione, 5-[2'-cyanobiphen-4-ylmethyl]-5-(4-methoxybenzenesulfonyl)thiazolidine-2,4-dione, 5-[3-(4-Methoxybenzyl)benzyl]-5-(4-methylbenzenesulfanyl)thiazolidine-2,4-dione, 5-[3-(2-Thiophen-2-yl[1,3]dioxolan-2-yl)benzyl]-5-(4-methylbenzenesulfanyl)thiazolidine-2,4-dione, 5-[3-(Thiophene-2-carbonyl)benzyl]-5-(4-methylbenzenesulfanyl)thiazolidine-2,4-dione, 5-Biphen-4-ylmethyl-5-(4-methoxybenzenesulfonyl)thiazolidine-2,4-dione, 5-(4'-Chlorobiphen-4-ylmethyl)-5-(4-methoxybenzenesulfonyl)thiazolidine-2,4-dione, 5-(4-Methoxybenzenesulfonyl)-5-(3'-(trifluoromethyl)biphen-4-ylmethyl)thiazolidine-2,4-dione, 5-(3',5'-Bis(trifluoromethyl)biphen-4-ylmethyl)-5-(4-methoxybenzenesulfonyl)thiazolidine-2,4-dione, 5-(2',4'-Dichlorobiphen-4-ylmethyl)-5-(4-methoxybenzenesulfonyl)thiazolidine-2,4-dione, 5-[3-(3-Chlorophenoxy)benzyl]-5-(4-methylbenzenesulfanyl)thiazolidine-2,4-dione, 5-[3-(2-thiophen-2-yl[1,3]dioxolan-2-yl)benzyl]-5-(4-methylbenzenesulfonyl)thiazolidine-2,4-dione and 2-[5-Benzyl-5-(4-methoxybenzenesulfonyl)2,4-dioxothiazolidin-3-yl]-acetic acid.

For the compounds defined above and referred to herein, unless otherwise noted, the following terms are explained.

"Halogen", as used herein means chloro, fluoro, bromo and iodo.

"Acyl" is the moiety —C(O)-alkyl of 1 to 12 carbon atoms.

"Alkyl" as used herein means a branched or straight chain having from 1 to 12 carbon atoms and more preferably from 1 to 6 carbon atoms. One or more of the carbon atoms may optionally be independently substituted with halogen optionally forming perfluoroalkyl. Exemplary alkyl groups include methyl, ethyl, propyl, isopropyl, butyl, isobutyl, t-butyl, pentyl and hexyl. Exemplary groups include trifluoromethyl.

"Alkenyl" as used herein means a branched or straight chain having from 2 to 12 carbon atoms and more preferably from 2 to 6 carbon atoms, the chain containing at least one carbon-carbon double bond. Alkenyl, may be used synonymously with the term olefin and includes alkylidenes. Exemplary alkenyl groups include ethylene, propylene and isobutylene.

"Alkoxy" as used herein means an alkyl-O group in which the alkyl group is as previously described. Exemplary alkoxy groups include methoxy, ethoxy, n-propoxy, i-propoxy, n-butoxy, and t-butoxy.

"Aryloxy" as used herein means an aryl-O group in which the aryl group is as previously described.

"Cycloalkyl" as used herein means a saturated ring having from 3 to 7 carbon atoms and more preferably from 3 to 6 carbon atoms. One or more of the carbon atoms may optionally be independently substituted with halogen optionally forming perfluorocycloalkyl. Exemplary cycloalkyl rings include cyclopropyl, cyclobutyl, cyclopentyl and cyclohexyl.

"Cycloalkoxy" as used herein means a cycloalkyl-O-group in which the cycloalkyl group is as previously defined.

"Carbamyl" is the moiety —C(O)NH$_2$.

"Aminocarbonyloxy" as used herein means the groups —N(H, alkyl of 1 to 12 carbon atoms, cycloalkyl of 3 to 7 carbon atoms or aryl of 6 to 12 carbon atoms)C(O)O-alkyl of 1 to 12 carbon atoms, —N(H, alkyl of 1 to 12 carbon atoms, cycloalkyl of 3 to 7 carbon atoms or aryl of 6 to 12 carbon atoms)C(O)O-cycloalkyl of 3 to 7 carbon atoms, or —N(H, alkyl of 1 to 12 carbon atoms, cycloalkyl of 3 to 7 carbon atoms or aryl of 6 to 12 carbon atoms)C(O)O-aryl of 6 to 12 carbon atoms.

"Aminocarbonylamino" as used herein means the groups —N(H, alkyl of 1 to 12 carbon atoms, cycloalkyl of 3 to 7 carbon atoms or aryl of 6 to 12 carbon atoms)C(O)N(H, alkyl of 1 to 12 carbon atoms, cycloalkyl of 3 to 7 carbon atoms or aryl of 6 to 12 carbon atoms) (H, alkyl of 1 to 12 carbon atoms, cycloalkyl of 3 to 7 carbon atoms or aryl of 6 to 12 carbon atoms), —N(H, alkyl of 1 to 12 carbon atoms, cycloalkyl of 3 to 7 carbon atoms or aryl of 6 to 12 carbon atoms)C(O)N(H, alkyl of 1 to 12 carbon atoms, cycloalkyl of 3 to 7 carbon atoms or aryl of 6 to 12 carbon atoms) alkyl of 1 to 12 carbon atoms, —N(H, alkyl of 1 to 12 carbon atoms, cycloalkyl of 3 to 7 carbon atoms or aryl of 6 to 12 carbon atoms)C(O)N(H, alkyl of 1 to 12 carbon atoms, cycloalkyl of 3 to 7 carbon atoms or aryl of 6 to 12 carbon atoms) aryl of 6 to 12 carbon atoms, or —N(H, alkyl of 1 to 12 carbon atoms, cycloalkyl of 3 to 7 carbon atoms or aryl of 6 to 12 carbon atoms)C(O)N(H, alkyl of 1 to 12 carbon atoms, cycloalkyl of 3 to 7 carbon atoms or aryl of 6 to 12 carbon atoms) cycloalkyl.

Aryl is defined as an optionally mono, di or tri-substituted aromatic hydrocarbon moiety having 6 to 12 ring atoms. Exemplary aryl groups include: phenyl, α-naphthyl, β-naphthyl, biphenyl, anthryl, tetrahydronaphthyl, phenanthryl, fluorenyl, and indanyl. Arylalkyl is an aryl substituted alkyl moiety wherein the alkyl chain is 1–6 carbon atoms (straight or branched). Arylalkyl moieties include benzyl, 1-phenylethyl, 2-phenylethyl, 3-phenylpropyl, 2-phenylpropyl and the like. Optional independently selected mono, di or tri-substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms.

Heteroaryl is defined as an optionally independently selected mono, di or tri-substituted aromatic heterocyclic ring system (monocyclic or bicyclic) having 5 to 12 ring atoms and from 1 to 4 heteroatoms independently selected from nitrogen, oxygen and sulfur. Preferred heteroaryl moieties are elected from: (1) furan, thiophene, indole, azaindole, oxazole, thiazole, isoxazole, isothiazole, imidazole, N-alkylimidazole, pyridine, pyrimidine, pyrazine, pyrrole, N-alkylpyrrole, pyrazole, N-alkylpyrazole, benzoxazole, benzothiazole, benzofuran, benzisoxazole, benzisothiazole, benzimidazole, N-alkylbenzimidazole, indazole, quinazoline, quinoline, and isoquinoline; (2) a bicyclic aromatic heterocycle where a phenyl, pyridine, pyrimidine or pyridizine ring is: (1) fused to a 6-membered aromatic (unsaturated) heterocyclic ring having one nitrogen atom; (2) fused to a 5 or 6-membered aromatic (unsaturated) heterocyclic ring having two nitrogen atoms; (3) fused to a 5-membered aromatic (unsaturated) heterocyclic ring having one nitrogen atom together with either one oxygen or one sulfur atom; or (4) fused to a 5-membered aromatic (unsaturated) heterocyclic ring having one heteroatom selected from O, N or S. Optional independently selected mono, di or tri-substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy.

"Phenyl" as used herein refers to a 6-membered aromatic ring.

"Sulfamoyl" as used herein refers to —SONH$_2$.

"sulfo" as used herein refers to —SO$_3$H.

Carbon number refers to the number of carbons in the carbon backbone and does not include carbon atoms occurring in substituents.

Where terms are used in combination, the definition for each individual part of the combination applies unless defined otherwise. For instance, perhaloalkoxy refers to an alkoxy group, as defined above, in which each hydrogen atom of the alkyl group has been replaced by a halogen. Further, perfluoroaryl refers to an aryl group as defined above in which each hydrogen of the aryl group has been replaced by a halogen.

It is understood by those practicing the art that the definition of compounds of Formula (I) when $R_1$, $R_2$, $R_3$, $R_4$, $R_5$, $R_6$ and $R_7$ contain asymmetric carbons, encompass all possible stereoisomers, mixtures and regioisomers thereof which possess the activity discussed below. Such regioisomers may be obtained pure by standard separation methods known to those skilled in the art. In particular, the definition encompasses any optical isomers and diastereomers as well as the racemic and resolved enantiomerically pure R and S stereoisomers as well as other mixtures of the R and S stereoisomers and pharmaceutically acceptable salts thereof, which possess the activity discussed below. Optical isomers may be obtained in pure form by standard separation techniques or enantiomer specific synthesis. It is understood that this invention encompasses all crystalline forms of compounds of Formula (I). The compounds of the present invention can be used in the form of salts derived from pharmaceutically or physiologically acceptable acids or bases. These salts include, but are not limited to, the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional pro-drug forms, which, when administered in such form, convert to the active moiety in vivo.

The present invention accordingly provides a pharmaceutical composition which comprises a compound of Formula (I) of this invention in combination or association with a pharmaceutically acceptable carrier. In particular, the present invention provides a pharmaceutical composition which comprises an effective amount of a compound of this invention and a pharmaceutically acceptable carrier.

Additionally, this invention provides a method of treatment, by administration of an effective amount of compounds of Formula (I), of ras oncogene-dependent tumors, which include cancers of the pancreas, colon, bladder, and thyroid; a method of controlling metastasis, suppressing angiogenesis, and inducing apoptosis; a method of treating Ras-associated proliferative diseases other than cancer, which include restenosis, neuro-fibromatosis, endometriosis, and psoriasis The compounds of Formula (I) may also inhibit prenylation of proteins other than Ras, and thus provide a method of treatment of diseases associated with other prenyl modifications of proteins.

The compounds of Formula (I) inhibit farnesyl-protein transferase and the farnesylation of the oncogene protein Ras. Thus, this invention further provides a method of inhibiting farnesyl protein transferase, (e.g., Ras farnesyl protein transferase) in mammals, especially humans, by the administration of an effective amount of the compounds of Formula (I). The administration of the compounds of this invention to patients, to inhibit farnesyl protein transferase, is useful in the treatment of the cancers and other diseases described below.

This invention provides a method for inhibiting or treating the abnormal growth of cells, including transformed cells by administering an effective amount of a compound of Formula (I). Abnormal growth of cells refers to cell growth independent of normal regulatory mechanisms (e.g., loss of contact inhibition). This includes abnormal growth of tumor cells (tumors) expressing an activated Ras oncogene; tumor cells in which the Ras protein is activated as a result of oncogenic mutation in another gene; and benign and malignant cells of other proliferative diseases in which aberrant Ras activation occurs.

This invention also provides a method for inhibiting or treating tumor growth by administering an effective amount of a compound of Formula (I), described herein, to a mammal (e.g., a human) in need of such treatment. In particular, this invention provides a method for inhibiting or treating the growth of tumors expressing an activated Ras oncogene by administration of an effective amount of a compound of Formula (I). Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

This invention also provides a method for inhibiting or treating proliferative diseases, both benign and malignant, wherein Ras proteins are aberrantly activated as a result of oncogenic mutation in other genes-i.e., the Ras gene itself is not activated by mutation to an oncogenic form-with said inhibition or treatment being accomplished by the administration of an effective amount of a compound of Formula (I), to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, Ick, and fyn), may be inhibited or treated by the compounds of Formula (I).

Additionally, this invention provides a method of inhibition or treating the abnormal growth of cells, by administration of an effective amount of compounds of Formula (I), of ras-oncogene-dependent tumors, which tumors include cancers of the pancreas, colon, bladder, and thyroid. Without wishing to be bound by theory, these compounds may function through the inhibition of G-protein function, such as ras p21, by blocking G-protein isoprenylation, thus making them useful in the treatment of proliferative diseases such as tumor growth and cancer. Without wishing to be bound by theory, the compounds of Formula (I) inhibit Ras farnesyl-protein transferase, and thus antiproliferative activity of ras-transformed cells and other prenyl modifications of proteins.

In another aspect, the invention provides a process for the preparation of a compound of Formula (I):

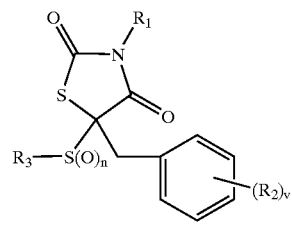

Formula (I)

wherein:
  $R_1$ is hydrogen;
  n is an integer of 0 or 2;
  v is an integer of 1 to 3;
  each $R_2$ is independently hydrogen, alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkyl(1 to 12 carbon atoms)amino, di(alkyl of 1 to 12 carbon atoms)amino, monoaryl(6 to 12 carbon atoms)amino, alkyl(1 to 12 carbon atoms)aryl(6 to 12 carbon atoms)amino, di(aryl of 6 to 12 carbon atoms) amino, monocycloalkyl(3 to 7 carbon atoms)amino, di(cycloalkyl of 3 to 7 carbon atoms)amino, alkyl(1 to 12 carbon atoms)cycloalkyl(3 to 7 carbon atoms) amino, aryl(6 to 12 carbon atoms)cycloalkyl(3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl(1 to 12 carbon atoms), carboxyaryl(6 to 12 carbon atoms), carboxycycloalkyl(3 to 7 carbon atoms), formyl, acyloxy of 1 to 12 carbon atoms, cyano, alkyl(1 to 12 carbon atoms)carbonyldioxy, aryl(6 to 12 carbon atoms)carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, monoalkyl(1 to 12 carbon atoms)carbamyl, di(alkyl of 1 to 12 carbon atoms) carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aminocarbonyloxy, aminocarbonylamino, or optionally when v is an integer of 1, the moiety

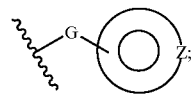

wherein the moiety

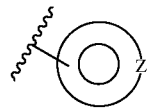

is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy and a moiety of the formula:

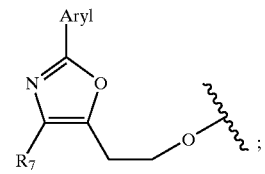

G is a single covalent bond, —O—, —S—, —SO—, —SO$_2$—, —N—R$_4$, —CH$_2$—, —CHOR$_4$, —CR$_8$OR$_4$, —C(OR$_5$)$_2$, —CO—, —CS—, —C=N—R$_6$ or moieties of the formulae:

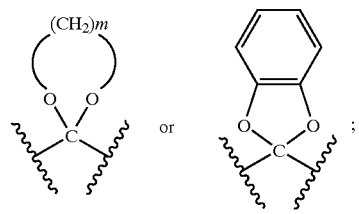

m is an integer of 2 to 4;

R$_3$ is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

or heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_4$ is hydrogen, alkyl of 1 to 12 carbon atoms, cycloalkyl of 3 to 7 carbon atoms, aryl of 6 to 12 carbon atoms optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

acyl of 1 to 12 carbon atoms, carboxyalkyl of 1 to 12 carbon atoms, carboxycycloalkyl of 3 to 7 carbon atoms, carboxyaryl of 6 to 12 carbon atoms wherein the aryl is optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms; formyl, carbamyl, monoalkyl(1 to 12 carbon atoms)carbamyl, di(alkyl of 1 to 12 carbon atoms)carbamyl, monoaryl(6 to 12 carbon atoms) carbamyl, di(aryl 6 to 12 carbon atoms)carbamyl, monocycloalkyl(3 to 7 carbon atoms)carbamyl, di(cycloalkyl 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, monoalkyl(1 to 12 carbon atoms)carboxyl, di(alkyl of 1 to 12 carbon atoms) carboxyl, monoaryl(6 to 12 carbon atoms)carboxyl, di(aryl 6 to 12 carbon atoms)carboxyl, monocycloalkyl(3 to 7 carbon atoms)carboxyl, di(cycloalkyl 3 to 7 carbon atoms)carboxyl, aryl(6 to 12 carbon atoms)alkyl(1 to 12 carbon atoms)carboxyl, cycloalkyl(3 to 7 carbon atoms)alkyl(1 to 12 carbon atoms)carboxyl, cycloalkyl(3 to 7 carbon atoms)aryl(6 to 12 carbon atoms) carboxylperfluoroaryl, monoalkyl(1 to 12 carbon atoms)thiocarbamyl, di(alkyl of 1 to 12 carbon atoms)thiocarbamyl, monoaryl(6 to 12 carbon atoms)thiocarbamyl, di(aryl 6 to 12 carbon atoms)thiocarbamyl, monocycloalkyl(3 to 7 carbon atoms)thiocarbamyl, di(cycloalkyl 3 to 7 carbon atoms) thiocarbamyl, aryl(6 to 12 carbon atoms)alkyl(1 to 12 carbon atoms)thiocarbamyl, cycloalkyl(3 to 7 carbon atoms)alkyl(1 to 12 carbon atoms) thiocarbamyl, or cycloalkyl(3 to 7 carbon atoms)aryl(6 to 12 carbon atoms)thiocarbamyl; heteroaryl of 5 to 12 ring atoms optionally substituted with 1 to 3 groups independently selected alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms) (cycloalkyl of 3 to 7 carbon atoms)amino, (aryl of 6 to 12 carbon atoms)(cycloalkyl of 3 to 7 carbon atoms) amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms)
carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_5$ is alkyl of 1 to 12 carbon atoms;

$R_6$ is alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, di(alkyl of 1 to 12 carbon atoms)amino, monoarylamino of 6 to 12 carbon atoms, alkyl(of 1 to 12 carbon atoms)aryl(of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, alkyl(of 1 to 12 carbon atoms)cycloalkyl (of 3 to 7 carbon atoms)amino, aryl(of 6 to 12 carbon atoms)cycloalkyl(of 3 to 7 carbon atoms)amino, arylsulfamoyl of 6 to 12 carbon atoms;

$R_7$ is alkyl of 1 to 12 carbon atoms;

$R_8$ is alkyl of 1 to 12 carbon atoms, cycloalkyl of 3 to 7 atoms and phenyl; and the pharmacologically acceptable salts thereof, comprising:

a) reacting a compound of the formula

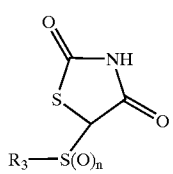

wherein $R_3$ and n are as defined above with a compound of formula

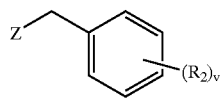

wherein $R_2$ and v are as defined above, and Z is a leaving group, preferably chloro, bromo, iodo, alkylsulfonyloxy of 1 to 10 carbon atoms, perfluoroalkylsulfonyloxy of 1 to 10 carbon atoms and phenylsulfonyloxy optionally substituted with from 1 to 3 substituents independently selected from halogen, alkyl of 1 to 10 carbon atoms, alkoxy of 1 to 10 carbon atoms, nitro and cyano in the presence of a base in an aprotic solvent to give a compound of Formula (I) and b) optionally converting a compound of formula (I) to a pharmaceutically acceptable salt.

DETAILED DESCRIPTION OF THE INVENTION

Synthesis:

Compounds of this invention are prepared according to the procedures described in the schemes below:

Scheme I

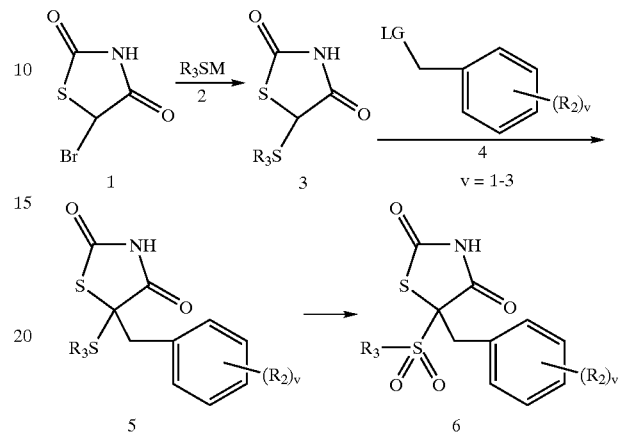

Refering to Scheme I, 5-bromothiazolidine-2,4-dione 1 (Zask, A., Jirkovsky, I., Nowicki, J. W., McCaleb, M. L. *J. Med. Chem.* 1990, 33,1418–1423) is allowed to react with an alkali metal anion of a thiol 2 where M is an alkali metal to give a 5-substituted-sulfanylthiazolidine-2,4-dione 3. Deprotonation of 5-substituted-sulfanylthiazolidine-2,4-dione 3 with two or more equivalents of a strong base such as lithium hexamethyldisilazide in an aprotic solvent such as N,N-dimethylformamide or tetrahydrofuran followed by the addition of an appropriate benzylic halide or sulfonate ester 4 where LG is a leaving group which includes halogen and p-toluenesulfonate provides the 5-substituted-sulfanyl-5-phenylmethylthiazolidine-2,4-diones 5. Selective oxidation of 5-substituted-sulfanyl-5-phenylmethylthiazolidine-2,4-diones 5 with a 2:1:1 mixture of potassium peroxymonosulfate ($KHSO_5$), potassium hydrogen sulfate ($KHSO_4$), and potassium sulfate $K_2SO_4$ in a low molecular weight alcohol solvent such as methanol provides the corresponding 5-substituted-sulfonyl-5 phenylmethylthiazolidine-2,4-diones 6.

Scheme II

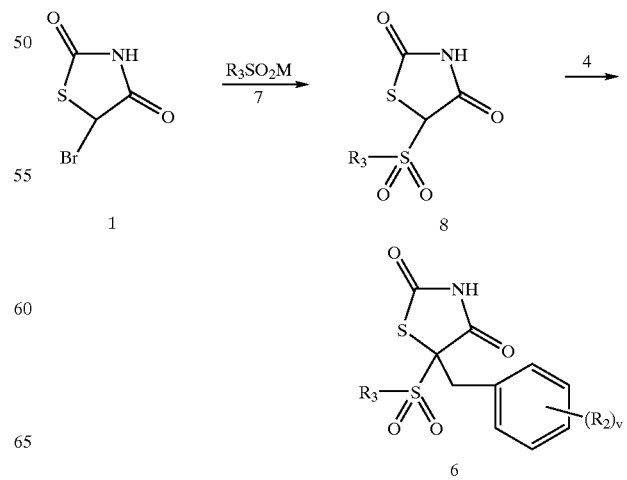

Refering to Scheme II, 5-bromothiazolidine-2,4-dione 1 is combined with one or more equivalents of an alkali metal arylsulfinate salt 7 where M is an alkali metal, in a polar, aprotic solvent such as tetrahydrofuran or N,N-dimethylformamide or a protic solvent such as a low molecular weight alcohol or water to provide the 5-substituted-sulfonylthiazolidine-2,4-diones 8. Deprotonation of 5-substituted-sulfonylthiazolidine-2,4-diones 8 with two or more equivalents of a strong base such as lithium hexamethyldisilazide in an aprotic solvent such as N,N-dimethylformamide (DMF)or tetrahydrofuran (THF) followed by the addition of an appropriate benzylic halide 4 where the leaving group (LG) is halo provides the 5-substituted-sulfonyl-5-phenylmethylthiazolidine-2,4-diones 6. Alkali metal arylsulfinate salts such as 7 where $R_3$ is hereinbefore defined, may be prepared for example from the corresponding readily available arylsulfonyl chlorides by treatment with sodium iodide in acetone (Harwood, L. M., Julia, M., Le Thuillier, G. *Tetrahedron* 1980, 36, 2483–2487).

Scheme III

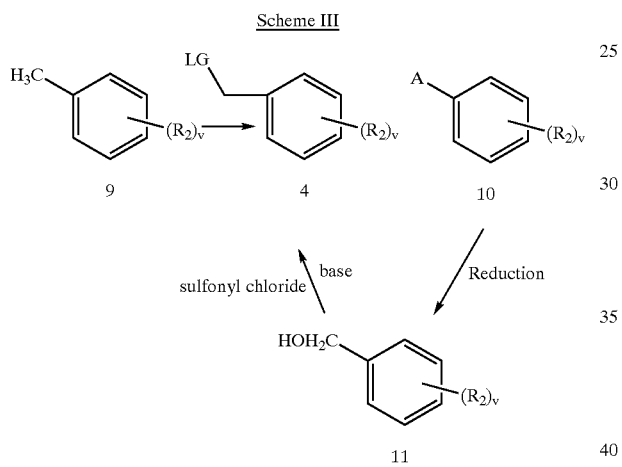

Refering to Scheme III, benzylic halides 4 where LG is a halide leaving group and which are not commercially available may be synthesized by benzylic halogenation of the corresponding toluene derivative 9 where v is an integer of 1 to 3 and $R_2$ is hereinbefore defined. For example, treatment of toluene derivative 9 with one or more equivalents of N-bromosuccinimide, a catalytic amount of benzoyl peroxide and light in an inert solvent such as carbon tetrachloride provides the benzylic bromide 4 (LG=Br). Alternatively an oxygenated derivative 10 in which A is an aldehyde, carboxylic acid or carboxylic ester can be reduced to the corresponding benzylic alcohol 11 by methods standard in the art which include but not limited to sodium borohydride in ethanol, lithium aluminum hydride in THF or dioxane, and borane in tetrahydrofuran. Commercially available or synthesized benzylic alcohol 11 can be converted to an appropriate sulfonate ester 4 where LG=—OSO$_2$alkyl of 1 to 12 carbon atoms or methyl substituted phenyl, by treatment with the corresponding sulfonyl chloride and a tertiary amine base such as triethylamine in a nonprotic solvent such as dichloromethane. The benzylic alcohols 11 can also be converted to the corresponding benzylic halides 4 (LG=Br) by treatment with carbon tetrabromide and triphenylphosphine in a nonreactive solvent such as tetrahydrofuran.

The preparation of benzylic halides 17 where G is

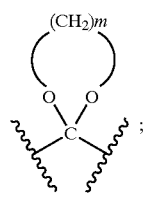

and $(R_2)_v$ with v=1 is

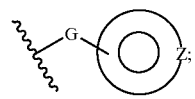

is shown in Scheme IV. Reaction of starting reagents 12 which are commercially available or readily available through literature synthesis and which include but are not limited to substituted and unsubstituted benzene, pyridine, thiophene, furan, quinoline and benzoxazole with metharylcarboxylic acid chloride 13 where G is —CO— in the presence of a Lewis acid catalyst such as aluminum chloride in an unreactive solvent such as dichloromethane or 1,2-dichloromethane to provide ketone 14. Reaction of ketone 14 with a 1,2-diol 15 where $R_5$ is hereinbefore defined by methods standard in the art provides ketal 16 which may be further brominated to give benzylic halide 17 which may then be added to 5-substituted-sulfanylthiazolidine-2,4-dione 3 using methods described in Scheme I.

Scheme IV

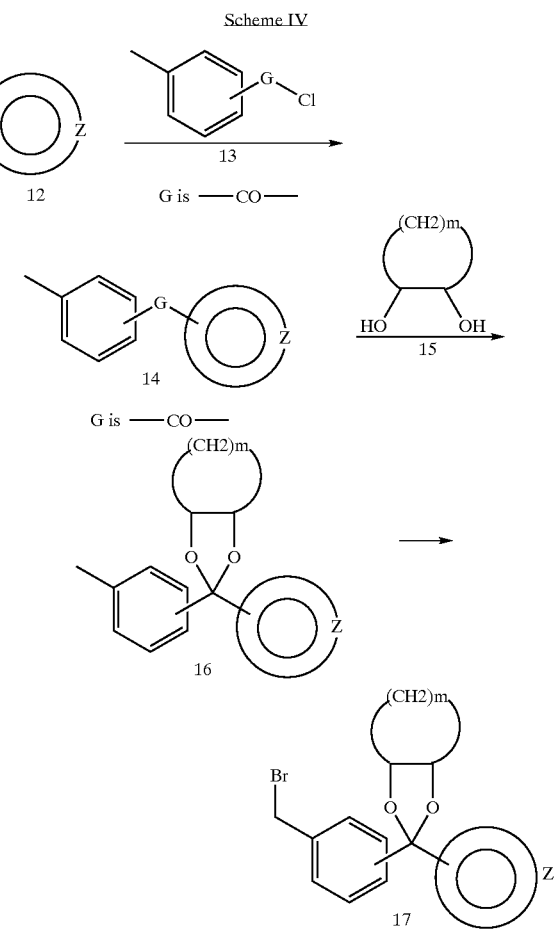

The preparation of analogs of ketone 14, not accessible via the Friedel-Crafts chemistry of Scheme IV are prepared using an alternative approach as shown in Scheme V. N-methoxy-N-methyl amides 19 of methylarylcarboxylic acids 18 are prepared by treating an appropriate activated derivative of the acid such as an acid chloride with N,O-dimethylhydroxylamine. Aryl or heteroaryl halides 20 (X'= Br, I) can be converted into an aryl or heteroarylmetal derivative 21 (M=Li, Mg) by metallation or halogen-metal exchange. Reaction of aryl or heteroarylmetal derivative 21 with N-methoxy-N-methyl amides 19 in an etherial solvent such as tetrahydrofuran affords, after acidification, ketones 14 (Nahm, S., Weinreb, S. M. *Tetrahedron Lett.*, 1981, 22, 3815–3818). Ketone 14 may be brominated to afford benzylic halides 22 using methods as described in Scheme III and then may be added to 5-substituted-sulfanylthiazolidine-2,4-dione 3 using the methods described in Scheme I.

Scheme V

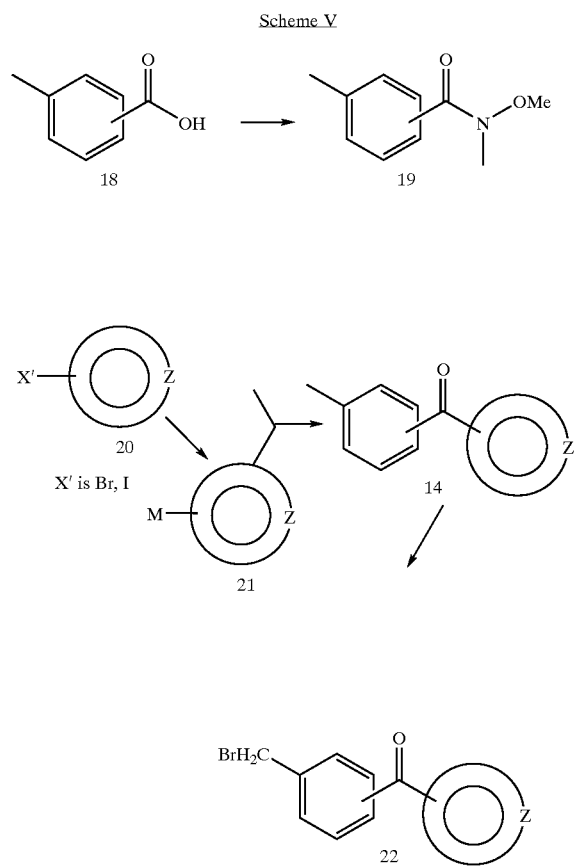

It will be appreciated that —G— as defined herein may undergo further chemical transformations. It will be further understood by those skilled in the art of organic synthesis that the various functionalities present on the molecule must be consistent with the chemical transformations proposed. This will frequently necessitate judgement as to the order of synthetic steps, protecting groups, if required, and deprotection conditions. Substituents which are compatible with the reaction conditions will be apparent to one skilled in the art. Additionally it will be further understood that chemical manipulations of —G— may best be performed on intermediates which include 14, rather than on the compounds of Formula (I). However, those skilled in the art may determine that a particular chemical transformation may best be performed on compounds of Formula (I). Specific non-limiting chemical transformations include:

a. when —G— is a carbonyl group (—C(O)—): reduction with $NaBH_4$ to an alcohol; reductive amination (for example $NHC_2H_5/Na(CN)BH_3$) to give a primary, secondary or tertiary amine; conversion to a thiocarbonyl with $P_2S_5$; conversion to an imine (for example $butylNH_2$/p-toluenesulfonic acid/molecular sieves); nucleophilic addition of an organometallic reagent (for example $CH_3MgBr$, butylLi, phenylMgBr, or phenylLi); and conversion to an acetal (for example $CH_3OH$/p-toluenesulfonic acid/molecular sieves); further chemical manipulations include:

b. when —G— is for example —C(H)(OH)— or —C(butyl)(OH): alkylation or acylation of the oxygen (for example butylBr or $CH_3COCl$); reduction to a methylene group c. —$CH_2$— (for example trifluroacetic acid/triethylsilane); and when —G— is d. —C(H)(NHbutyl): alkylation or acylation of the nitrogen (for example butylBr or $CH_3COCl$), and conversion of the amine to a carbamate, urea, or thiourea (for example $C_2H_5OCOCl$. $C_2H_5NCO$, or $C_2H_5NCS$).

As shown in Scheme VI, 5-substituted-sulfonyl-5-phenylmethylthiazolidine-2,4-diones 6 may be alkylated with $R_1Br$ where $R_1$ is hereinbefore defined provided $R_1$ is not H using bases such as potassium carbonate, sodium hydride in acetone, THF or DMF affords N-substituted derivative 23. For example, in the case where $R_1$ is —$CH_2$—C(O)—$OR_9$ and $R_9$ is alkyl of 1 to 6 carbon atoms, base hydrolysis affords acid 24. Reaction of acid 24 with 1-hydroxybenzotriazole (HOBT) and 1-[3-(dimethylamino)propyl]-3-ethylcarbodiimide hydrochloride (DAEC) affords benzyl substituted 25 which may be reduced with $H_2$, Pd/C to afford hydroxyl amine 26.

Scheme VI

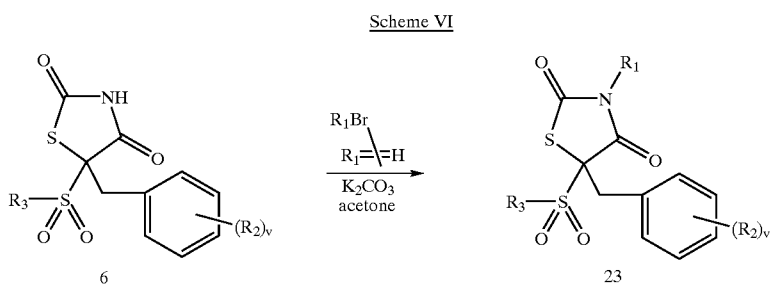

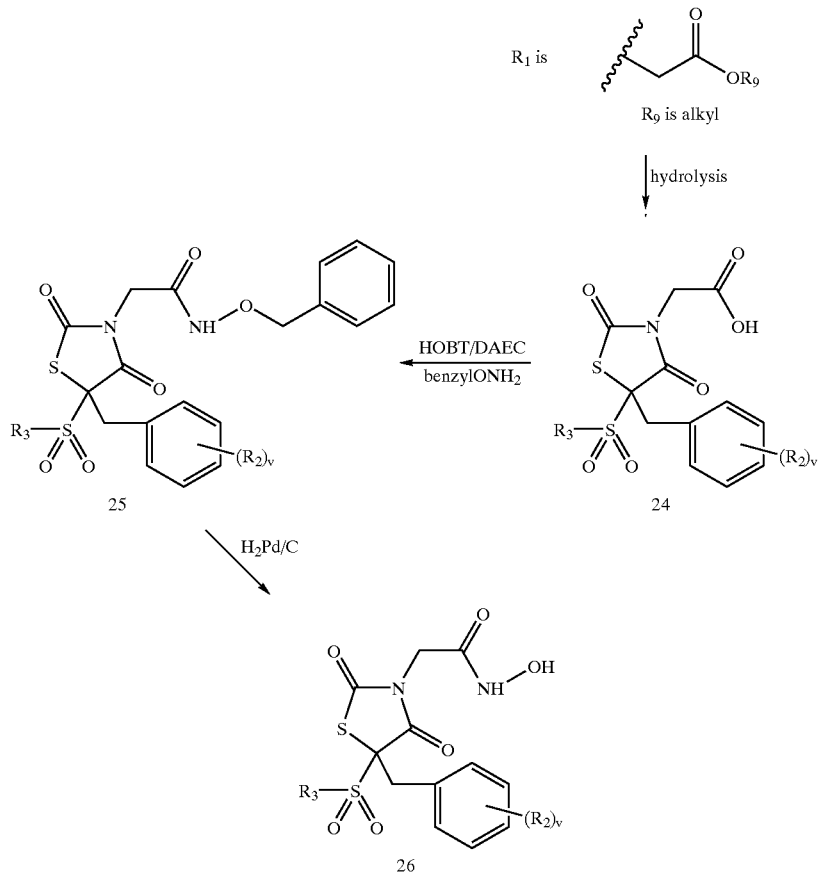

Standard Pharmacological Test Procedures

The ability of the compounds of this invention to inhibit FPTase was evaluated in the standard pharmacological in vitro test procedures described below. Data for representative examples is summarized in Table I.

Enzyme assay: FPTase inhibition in vitro assay was performed according to James, G. L., Brown, M. S., and Goldstein, J. L., *Methods in Enzymology*, 1995, 255, 38–46; and Garcia, M. A., et al., *J. Biol. Chem.*, 1993, 268, 18415–18420.

Materials—Purified FPTase (Moomaw, J. F. and Casey, P. J., *J. Biol. Chem.*, 1992, 267, 17438–17443), purified $His_6$-Ras, inhibitor compounds at 10 mg/ml or 10 mM in 100% DMSO, $^3$H-FPP (50,000 dpm/pmol) Amersham, TCA/SDS (6%/2%), TCA (6%), Glass fiber filters (0.22–0.45 m), vacuum manifold or 96 well filtration plates.

Methods—1. Dilute FPTase inhibitors from stock solutions to 2.5× in 2.5% DMSO, 10 mM DTT, 0.5% octyl-B-glucoside. 2. Solution #1 is added to FPTase reaction in a volume of 20 ml. 3. Standard reaction mix, 50 ml, contains 50 mM Tris (7.5),10 mM $ZnCl2$, 3 mM $MgCl2$, 20 mM KCl, 5 mM DTT, 0.2% octyl-B-glucoside, 1% DMSO, 40 mM $His_6$-Ras, 10 ng FPTase, and various concentrations of FPTase inhibitors. 4. Incubate for 30–90 min at 25° C. 5. Stop reactions with TCA/SDS (6%/2%), hold at 4° C. for 45–60 min. 6. Filter by manifold or 96 well plate, wash filter 3–5× with TCA (6%). 7. Add scintillant to filters, measure $^3$H-FPP incorporation into Ras protein.

Analysis of Results—Percent inhibition by test compounds is determined by the following:

(cpm from precipitated Ras with test compounds)–(background cpm)×100=% inhibition.

(cpm from precipitated Ras without test compounds)–(background cpm)

Cell-based assays: Tumor inhibition in vitro assay was performed according to P. Skehan, R. Storeng, D. Scudiero, A. Monks, J. McMohan, D. Vistica, J. Warren, H. Bokesh, S. Kenney, and M. R. Boyd, *J. Natl. Cancer Instit.*, 1990, 82 (13), 1107–1112; L. V. Rubinstein, R. H. Shoemaker, K. D. Paull, R. M. Simon, S. Tosini, P. Skehan, D. A. Scudiero, A. Monks, and M. R. Boyd, *J. Natl. Cancer Instit.*, 1990, 82 (13), 1113–1118; A. Monks, et al., *J. Natl. Cancer Instit.*, 1991, 83, 757–766; M. R. Boyd and K. D. Paull, *Drug Development Res.*, 1995, 34, 91–109; and S. P. Fricker and R. G. Buckley, *Anticancer Research*, 1996, 16, 3755–3760.

Materials—Cell Lines: Human tumor cell lines DLD-1 and LoVo; ras-transformed rat fibroblast cell lines, RAT-H-ras and RAT-K-ras (growth inhibited by standard FPTase inhibitors), and the parent cell line RAT-2 (resistant to standard FPTase inhibitors). Cell Media: RPMI 1640 (or DMEM medium and McCoy's medium) with 10% Fetal Bovine Serum supplemented with L-glutamine and Pennicilin/Streptomycin. Compounds: Supplied usually as a 10 mM stock in 100% DMSO. Normal Saline: 150 mM NaCl Trichloroacetic Acid (TCA): 50% (w/v) in water. Sulforhodamine (SRB): 0.4% (w/v) in 1% Acetic Acid. Tris Base: 10 mM in water.

Methods—Cells are plated at 2000 cells per well, per 200 ml media, and allowed to adhere overnight at 37° C. At 24 h post plating, compounds are added directly at a volume of 0.5 ml. Compound is first diluted in DMSO to generate concentrations of compound or reference standard of: 1, 5, 10 and 25 mM. Dilutions can be made in an identical 96 well plate so that compounds can be added using a multichannel micropipettor set at 0.5 ml. The cells are then incubated for four days after which the media is removed using a 12 well manifold by first tipping the plate forward at a 45 degree angle and then inserting the manifold in an upright orientation to prevent the tips of the manifold from disturbing cells at the bottom of the plate. 200 ml of normal saline is then added to each well using an 8 well multichannel pipettor, followed by the careful addition of 50 ml of 50% TCA. The plates are then incubated for 2 h at 4° C., after which the supernatant is removed using the same technique as above and the plates washed twice with 200 ml water. The plates are then air dried and 50 ml of SRB stock solution is carefully added so that the entire bottom of each well is covered. This again can be used using an 8 well multichannel pipettor. The SRB is incubated with fixed cells for 15 min at room temperature, after which the SRB is removed with the manifold as described above and the plates washed twice with 350 ml of 1% acetic acid per well each time. The plates are then air dried after which the bound SRB is released from protein by the addition of 200 ml of Tris base. Resolubilizing the SRB is aided by placing the plates on a rotator for 15–30 min. The absorbance of each well is determined at 550 or 562 nm using a microtiter plate reader. Analysis of Results—Each compound or dilution thereof is performed in triplicate. Outliers are identified by visual inspection of the data. Each plate should have a control (vehicle only). A standard curve is constructed by plotting the concentration of compound against the average absorbance calculated at that concentration. A curve is plotted and the concentration at which the curve passes through the 50% absorbance mark seen in the control well is the $IC_{50}$ calculated for that compound.

TABLE I in vitro FTase Inhibition Assay

| Example # | Activity* $\mu M$ |
|---|---|
| 1 | 2.25 |
| 2 | 6.5 |
| 3 | (1%) |
| 4 | (1%) |
| 5 | (-2%) |
| 6 | (21%) |
| 7 | 2.5 |
| 8 | 1.3 |
| 9 | 1.2 |
| 10 | 4.25 |
| 11 | 2.5 |
| 12 | 3.7 |
| 13 | (28%) |
| 14 | 0.077 |
| 15 | (4%) |
| 16 | 0.35 |
| 17 | 2.9 |
| 18 | 4.5 |
| 19 | 2.8 |
| 20 | 1.7 |
| 21 | 1 |
| 22 | 2.5 |
| 23 | >10 |
| 24 | 0.74 |
| 25 | 3.5 |
| 26 | 6 |

*IC50 or (% inhib. at 10 $\mu M$) with H-Ras as substrate for farnesylation

Compounds of this invention were also tested with K-Ras as the substrate for farnesylation with observed activities of 2.5 $\mu M$ to >10 $\mu M$. Compounds were additionally tested in cell-based assays against human tumor cell lines DLD-1 and LoVo and ras-transformed rat fibroblast cell lines, RAT-H-ras and RAT-K-ras, and the parent cell line RAT-2, as described under Assays. The range observed for inhibition of cell growth was $IC_{50}$=9 to >40 $\mu M$.

Based on the results of these sstandard pharmacological test procedures, the compounds of this invention are useful as agents for treating, inhibiting or controlling ras-associated diseases by inhibiting farnesyl-protein transferase enzyme, when administered in amounts ranging from about 10 to about 200 mg/kg of body weight per day. A preferred regimen for optimum results would be from about 10 mg to about 100 mg/kg of body weight per day and such dosage units are employed that a total of from about 100 mg to about 1000 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agnet such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures therof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and starage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

The present invention accordingly provides a pharmaceutical composition which comprises a compound of Formula (I) of this invention in combination or association with a pharmaceutically acceptable carrier. In particular, the present invention provides a pharmaceutical composition which comprises an effective amount of a compound of this invention and a pharmaceutically acceptable carrier.

As used in accordance with this invention, the term providing an effective amount of a compound means either directly administering such compound, or administering a prodrug, derivative, or analog which will form an effective amount of the compound within the body.

The invention will be more fully described in conjunction with the following specific examples which are not to be construed as limiting the scope of the invention.

EXAMPLE 1

5-(4-[2-(5-Methyl-2-phenyloxazol-4-yl)ethoxy] benzyl)-5-(4-methylbenzenesulfonyl)thiazolidine-2, 4-dione Prepared analogously to Example 9. m.p. 202–204° C.

EXAMPLE 2

5-(4-Bromo-2-fluorobenzyl)-5-(4-methylbenzenesulfonyl)thiazolidine-2,4-dione

Prepared analogously to Example 9. m.p. 236–237° C.

EXAMPLE 3

5-(3,4-Dichlorobenzyl)-5-(4-methylbenzenesulfonyl) thiazolidine-2,4-dione

Prepared analogously to Example 9. m.p. 183–184° C.

EXAMPLE 4

5-(4-Bromo-2-fluorobenzyl)-5-(naphthalene-2-sulfonyl)thiazolidine-2,4-dione

Prepared analogously to Example 9. m.p. 195–197° C.

EXAMPLE 5

5-(4-[2-(5-Methyl-2-phenyloxazol-4-yl)ethoxy] benzyl)-5-(naphthalene-2-sulfonyl)thiazolidine-2,4-dione Prepared analogously to Example 9. m.p. 133–136° C.

EXAMPLE 6

5-Benzyl-5-(4-methoxybenzenesulfonyl) thiazolidine-2,4-dione

Prepared analogously to Example 9. m.p. 146–152° C. $^1$H NMR (DMSO): δ 12.70 (br s, 1H),

EXAMPLE 7

2-[5-Benzyl-5-(4-methoxybenzenesulfonyl)-2,4-dioxothiazolidin-3-yl]-N-hydroxyacetamide To a solution of 2-[5-Benzyl-5-(4-methoxybenzenesulfonyl)-2,4-dioxothiazolidin-3-yl]-acetic acid (Example 27) (0.400 g, 0.92 mmol) in 13 mL of dichloromethane was added 1-hydroxybenzotriazole (0.126 g, 0.93 mmol), 4-methylmorpholine (0.506 g, 5.00 mmol), O-benzylhydroxylamine hydrochloride (0.440 g, 2.76 mmol), and 1-[3-(Dimethylamino)propyl]-3-ethylcarbodiimide hydrochloride (0.232 g, 1.21 mmol) and the mixture was stirred at room temperature for 24 hours under a nitrogen atmosphere. The mixture was diluted with 50 mL of dichloromethane and washed with 2×100 mL of water. The combined aqueous washings were back extracted with 100 mL of dichloromethane and the combined organic phases were washed with 100 mL of brine, dried over anhydrous $Na_2SO_4$ and concentrated in vacuo. Column chromatography provided 0.280 g of 2-[5-Benzyl-5-(4-methoxybenzenesulfonyl)-2,4-dioxothiazolidin-3-yl]-N-benzyloxyacetamide as a colorless foam. This material was dissolved in 25 mL of dioxane and stirred at room temperature under a hydrogen atmosphere with an excess of 10% Pd on carbon for 2 days. The mixture was filtered through a celite pad washing with dioxane, followed by ethyl acetate, then methanol. The combined filtrates were concentrated in vacuo and column chromatography provided 0.050 g of the title compound as a white powder. m.p. 81–85° C.

EXAMPLE 8

5-(3-[2-(4-Methoxyphenyl)[1,3]dioxolan-2-yl] benzyl)-5-(4-methylbenzenesulfanyl)thiazolidine-2, 4-dione A solution of 5-(4-methylbenzenesulfanyl)thiazolidine-2, 4-dione (0.239 g, 1.00 mmol) (Wrobel, J., Zenan, L., Dietrich, A., McCaleb M., Mihan, B., Sredy J. Sullivan, D. J. Med. Chem. 1998, 41 1084–1091) in 3 mL of 1,2-dimethyoxyethane (DME) under an argon atmosphere was cooled to 0° C. and a 1.0 M solution of sodium hexamethyldisilylazide in tetrahydrofuran was added. The mixture was stirred 1 h at 0° C. and a solution of 2-[3-(bromomethyl) phenyl]-2-(4-methoxyphenyl)-1,3-dioxolane (0.528 g (75% pure) 1.13 mmol) in a small volume of DME was added. The mixture was stirred 1 h at 0° C. and then partitioned between diethyl ether (100 mL) and dilute HCl solution (100 mL). The organic phase was dried over anhydrous $MgSO_4$, the solvent was removed in vacuo, and the residue was crystallized from petroleum ether/diethyl ether to give 0.221 g (44% yield) of the title compound as colorless prisms. $^1$H NMR: δ 7.15–7.47 (m, 11H), 6.83 (dd, J=6.8, 1.9 Hz, 2H), 3.96–4.10 (m, 4H), 3.78 (s, 3H), 3.66 (A of AB, J=13.9 Hz, 1H), 3.32 (B of AB, J=13.9 Hz, 1H), 2.36 (s, 3H). $^{13}$C NMR: δ 173.2, 167.0, 159.3, 142.6, 141.4, 137.3, 134.0, 133.5, 130.3, 130.1, 128.7, 128.4, 127.6, 126.0, 124.8, 113.5, 109.1, 72.9, 64.9, 55.3, 43.3, 21.4. MS (m/e): 508.4 (M+H)$^+$. Anal: Calc for $C_{27}H_{25}NO_5S_2$:63.89% C, 4.96%H, 2.76% N; Found: 63.67% C, 5.03% H, 2.53% N.

EXAMPLE 9

5-(3-[2-(4-Methoxyphenyl)[1,3]dioxolan-2-yl]
benzyl)-5-(4-methylbenzenesulfonyl)thiazolidine-2,
4-dione Prepared analogously to Example 8 from 5-(4-methylbenzenesulfonyl)thiazolidine-2,4-dione (Wrobel, J., Zenan, L., Dietrich, A., McCaleb M., Mihan, B., Sredy J. Sullivan, D. *J. Med. Chem.* 1998, 41 1084–1091). Column chromatography provided a light yellow foam. $^1$H NMR: δ 7.85 (dd, J=6.8, 1.6 Hz, 2H), 7.61 (d, J=8.2 Hz, 1H), 7.22–7.45 (m, 7H), 7.08 (d, J=7.0 Hz, 1H), 6.82 (dd, J=6.8, 2.0 Hz, 2H), 3.96–4.08 (m, 4H), 3.90 (a of ab, J=13.6 Hz, 1H), 3.78 (s, 3H), 3.33 (b of ab, J=13.6 Hz, 1H), 2.49 (s, 3H). MS (m/e): 540.3 (M+H)$^+$.

EXAMPLE 10

5-(3-(4-methoxybenzoyl)benzyl)-5-(4-methylbenzenesulfonyl)thiazolidine-2,4-dione During chromatographic purification of 5-(3-[2-(4-methoxyphenyl)[1,3]dioxolan-2-yl]benzyl)-5-(4-methylbenzenesulfonyl)thiazolidine-2,4-dione (Example 9) the deketalized product was isolated as a yellow foam. $^1$H NMR: δ 7.88 (br s), 1H, 7.87 (d, J=8.4 Hz, 2H), 7.74–7.79 (m, 2H), 7.67 (dt, J=6.9, 1.8 Hz, 1H), 7.53 (s, 1H), 7.36–7.44 (m, 4H), 6.92–6.99 (m, 2H), 3.99 (A of AB, J=13.8 Hz, 1H), 3.90 (s, 3H), 3.41 (B of AB, J=13.8 Hz, 1H), 2.50 (s, 3H). MS (m/e): 496.4 (M+H)$^+$.

EXAMPLE 11

5-(3-(4-methoxybenzoyl)benzyl)-5-(4-methylbenzenesulfanyl)thiazolidine-2,4-dione Prepared analogously to example 19 from 5-(3-(4-methoxybenzoyl)benzyl)-5-(4-methylbenzenesulfonyl)thiazolidine-2,4-dione (Example 10). Column chromatography provided a colorless foam. $^1$H NMR: δ 7.78–7.82 (m, 2H), 7.72 (dt, J=7.2, 1.6 Hz, 1H), 7.65 (br s, 1H), 7.41–7.50 (m, 4H), 7.18 (d, J=7.9 Hz, 2H), 6.97 (dd, J=2.1, 6.9 Hz, 2H), 3.89 (s, 3H), 3.72 (A of AB, J=14.0 Hz, 1H), 3.39 (B of AB, J=14.0 Hz, 1H), 2.36 (s, 3H). MS (m/e): 464.4 (M+H)$^+$.

EXAMPLE 12

5-(3-[Hydroxy(4-methoxyphenyl)methyl]-benzyl)-5-(4-methylbenzenesulfanyl)thiazolidine-2,4-dione To a solution of 5-(3-(4-methoxybenzoyl)benzyl)-5-(4-methylbenzenesulfanyl)thiazolidine-2,4-dione (Example 11) (0.150 g, 0.32 mmol) in 1 mL of anhydrous ethanol was added NaBH$_4$ (0.015 g, 0.39 mmol) and the mixture was stirred 15 h at room temperature under an argon atmosphere. It was then partitioned between diethyl ether (50 mL) and dilute HCl solution (50 mL) with care to prevent excess foaming as residual NaBH$_4$ decomposed. The organic phase was dried over anhydrous MgSO$_4$, and the solvent was removed in vacuo. Column chromatography provided 0.105 g (75% yield) of the title compound as a colorless foam. $^1$H NMR: δ 7.46 (d, J=8.0 Hz, 2H), 7.45 (s, 1H), 7.15–7.33 (m, 7H), 6.84–6.88 (m, 2H), 5.78 (br s, 1H), 3.78 (s, 3H), 3.64 & 3.65 (diastereomeric pair, A of AB, J=13.9 Hz, 1H), 3.29 & 3.30 (diastereomeric pair, B of AB, J=13.9 Hz, 1H), 2.36 (s, 3H), 2.25 (br s, 1H). MS (m/e): 448.3 (M–OH)$^+$.

EXAMPLE 13

5-(4-Bromobenzyl-5-(4-methylbenzenesulfonyl)
thiazolidine-2,4-dione

Prepared analogously to Example 9 from 4-bromobenzyl bromide. Column chromatography provided pale yellow microplates. $^1$H NMR (DMSO): δ 12.70 (br s, 1H), 7.82 (d, J=8.4 Hz, 2H), 7.56 (d, J=8.4 Hz, 2H), 7.52 (d, J=8.4 Hz, 2H), (d, J=8.4 Hz, 2H), 3.69 (A of AB, J=13.6 Hz, 1H), 3.48 (B of AB, J=13.6 Hz, 1H), 2.46 (s, 3H). $^{13}$C NMR: δ 169.2, 167.6, 146.8, 132.9, 131.6, 131.3, 130.9, 129.9, 121.3, 85.3, 54.8, 21.2. MS (m/e): 438.2 and 440.3 (M–H)$^-$ Br isotopes. Anal: Calc for C$_{17}$H$_{14}$BrNO$_4$S$_2$: 46.37% C, 3.20% H, 3.18% N; Found: 45.98% C, 3.40% H, 3.28% N.

EXAMPLE 14

5-[2'-cyanobiphen-4-ylmethyl]-5-(4-methylbenzenesulfonyl)thiazolidine-2,4-dione

Prepared analogously to Example 9 from from 4'-bromomethyl-2-cyanobiphenyl in N,N-dimethylformamide. Column chromatography provided a colorless glass. $^1$H NMR: δ 8.06 (d, J=8.4 Hz, 2H), 7.82 (br s, 1H), 7.75 (dd, J=7.7, 1.0 Hz, 1H), 7.65 (dt, J=1.4, 7.7 Hz, 1H), 7.41–7.50 (m, 6H), 4.00 (A of AB, J=13.7 Hz, 1H), 3.42 (B of AB, J=13.7 Hz, 1H), 2.50 (s, 3H). MS (m/e): 463.1 (M+H)$^+$.

EXAMPLE 15

5-[2'-(1H-Tetrazol-5-yl)biphen-4-ylmethyl]-5-(4-methylbenzenesulfonyl)thiazolidine-2,4-dione Prepared analogously to Example 9 using N-(Triphenylmethyl)-5-[2-[4'-(bromomethyl)biphenylyl]] tetrazole (Schoen, W. R.; Pisano, J. M.; Prendergast, K.; Wyvratt, M. J., Jr.; Fisher, M. H.; Cheng, K.; Chan, W.-S.; Butler, B.; Smith, R. G.; Ball, R. G. *J. Med. Chem.* 1994, 37, 897–906.)

$^1$H NMR: δ 8.06 (d, J=7.3 Hz, 1H), 7.88 (d, 8.3 Hz, 2H), 7.52–7.63 (m, 2H), 7.41–7.46 (m, 3H), 7.23–7.26 (m, 2H), 7.12 (d, J=8.1 Hz, 2H), 3.94 (A of AB, J=13.6 Hz, 1H), 3.46 (B of AB, J=13.6 Hz,1H), 2.51 (s, 3H). MS (m/e): 506.2 (M+H)$^+$.

EXAMPLE 16

5-[2'-cyanobiphen-4-ylmethyl]-5-(4-methoxybenzenesulfonyl)thiazolidine-2,4-dione Prepared analogously to Example 9 from from 5-(4-methoxybenzenesulfonyl)thiazolidine-2,4-dione and 4'-bromomethyl-2-cyanobiphenyl in N,N-dimethylformamide. Trituration with diethyl ether provided an off-white solid. $^1$H NMR: δ 7.93 (dd, J=7.0, 2.0 Hz, 2H), 7.75 (dd, J=7.7, 1.0 Hz, 1H), 7.64 (dt, J=1.3, 7.7 Hz, 1H), 7.42–7.50 (m, 4H), 7.31 (d, J=8.3 Hz, 2H), 7.07 (dd, J=7.1, 1.9 Hz, 2H), 4.00 (A of AB, J=13.7 Hz, 1H), 3.93 (s, 3H), 3.42 (B of AB, J=13.7 Hz, 1H) MS (m/e): 477.3 (M–H)$^+$. Anal: Calc for C$_{24}$H$_{18}$N$_2$O$_5$S$_2$.0.167 C$_3$H$_9$NO: 59.92% C, 4.00% H, 6.18% N; Found: 59.60% C, 4.04% H, 5.99% N.

EXAMPLE 17

5-[3-(4-Methoxybenzyl)benzyl]-5-(4-methylbenzenesulfanyl)thiazolidine-2,4-dione

To a solution of 5-(3-(4-methoxybenzoyl)benzyl)-5-(4-methylbenzenesulfanyl)thiazolidine-2,4-dione (0.100 g, 0.22 mmol) (Example 11) in 0.5 mL of trifluoroacetic acid under an argon atmosphere was added triethylsilane (0.055 g 0.47 mmol) and the solution was stirred 200 min at room temperature. An additional portion of triethylsilane (0.028 g, 0.24 mmol) was then added and the solution was stirred an additional 90 min at room temperature. The volatile materials were then removed in vacuo. Column chromatography provided, in addition to a like quantity of silane contaminated material, 0.041 g (42% yield) of pure title compound as a colorless foam. $^1$H NMR: δ 7.48 (br s, 1H), 7.46 (d, J=8.4 Hz, 2H), 7.06–7.24 (m, 6H), 7.05 (d, J=8.4 Hz, 2H), 6.81–6.84 (m, 2H), 3.90 (s, 2H), 3.77 (s, 3H), 3.62 (A of AB, J=14.0 Hz, 1H), 3.27 (B of AB, J=14.0 Hz, 1H), 2.35 (s, 3H). $^{13}$C NMR: δ 173.4, 167.4, 158.0, 141.9, 141.4, 137.3, 133.8, 131.2, 130.1, 129.8, 128.6, 128.5, 128.4, 124.8, 113.9, 72.8, 55.3, 43.2, 40.8, 21.4. MS (m/e): 448.1 (M−H)$^-$.

EXAMPLE 18

5-[3-(2-Thiophen-2-yl[1,3]dioxolan-2-yl)benzyl]-5-(4-methylbenzenesulfanyl)thiazolidine-2,4-dione Prepared analogously to Example 8 from 2-[3-(bromomethyl)phenyl]-2-(2-thienyl)-1,3-dioxolane. Column chromatography provided a colorless foam. $^1$H NMR: δ 7.46–7.61 (m, 4H), 7.23–7.32 (m, 3H), 7.17 (d, J=8.0 Hz, 2H), 6.90 (dd, J=5.0, 3.6, Hz, 1H), 6.81 (dd, J=3.6, 1.2 Hz, 1H), 4.14–4.22 (m, 2H), 3.95–4.08 (m, 2H), 3.68 (A of AB, J=13.9 Hz, 1H), 3.34 (B of AB, J=13.9 Hz, 1H), 2.36 (s, 3H). $^{13}$C NMR: δ 173.4, 167.3, 146.0, 141.7, 141.4, 137.3, 133.7, 130.7, 130.1, 128.7, 128.5, 126.6, 126.3, 125.8, 124.8, 107.4, 72.7, 65.2, 43.2, 21.4. MS (m/e): 483.9 (M+H)$^+$.

EXAMPLE 19

5-[3-(Thiophene-2-carbonyl)benzyl]-5-(4-methylbenzenesulfanyl)thiazolidine-2,4-dione A solution of 5-[3-(2-thiophen-2-yl[1,3]dioxolan-2-yl)benzyl]-5-(4-methylbenzenesulfanyl)thiazolidine-2,4-dione (Example 18) (0.593 g, 1.23 mmol) was dissolved in 15 mL of acetone under a nitrogen atmosphere and 0.064 g, 0.25 mmol) of pyridinium p-toluenesulfonate was added, followed by 1.5 mL of water. The mixture was warmed to reflux under a nitrogen atmosphere for 46 h then allowed to stir at room temperature for 24 h. The solvents were removed from the mixture by rotary evaporation and the residue was partitioned between diethyl ether (60 mL) and dilute HCl solution (50 mL). The organic phase was dried over anhydrous MgSO$_4$, and the solvent was removed in vacuo. Column chromatography provided (0.375 g, 70% yield) of the title compound as a colorless foam. $^1$H NMR: δ 7.81 (d, J=7.6 Hz, 1H), 7.78 (s, 1H), 7.73 (d, J=5.2 Hz, 1H), 7.70 (br s, 1H), 7.66 (d, J=3.6 Hz, 1H), 7.44–7.53 (m, 4H), 7.16–7.19 (m, 3H), 3.73 (A of AB, J=14.0 Hz, 1H), 3.42 (B of AB, J=14.0 Hz, 1H), 2.36 (s, 3H). $^{13}$C NMR: δ 187.7, 173.2, 167.0, 143.4, 141.6, 138.4, 137.3, 135.0, 134.6, 134.5, 134.1, 131.6, 130.2, 128.8, 128.1, 124.5, 72.4, 42.9, 21.4. MS (m/e): 440.0 (M+H)$^+$. Anal: Calc for C$_{22}$H$_{17}$NO$_3$S$_3$: 60.11% C, 3.90% H, 3.19% N; Found: 59.87% C, 3.96% H, 3.12% N.

EXAMPLE 20

5-Biphen-4-ylmethyl-5-(4-methoxybenzenesulfonyl)thiazolidine-2,4-dione

Prepared analogously to Example 9 from from 5-(4-methoxybenzenesulfonyl)thiazolidine-2,4-dione and 4-(bromomethyl)biphenyl in N,N-dimethylformamide. Trituration with diethyl ether provided an off-white solid. $^1$H NMR: δ 7.98 (s, 1H), 7.93, (dd, J=7.0, 2.0 Hz, 2H), 7.34–7.57 (m, 7H), 7.23–7.26 (m, 2H), 7.06 (dd, J=7.0, 2.0 Hz, 2H), 3.97 (A of AB, J=13.7 Hz, 1H), 3.92 (s, 3H), 3.39 (B of AB, J=13.7 Hz, 1H). MS (m/e): 452.1 (M−H)$^-$. Anal: Calc for C$_{23}$H$_{19}$NO$_5$S$_2$.C$_3$H$_7$NO: 59.30% C, 4.98% H, 5.32% N; Found: 59.13% C, 4.89% H, 5.24% N. MP: 119–122° C.

EXAMPLE 21

5-(4'-Chlorobiphen-4-ylmethyl)-5-(4-methoxybenzenesulfonyl)thiazolidine-2,4-dione Prepared analogously to Example 9 from from 5-(4-methoxybenzenesulfonyl)thiazolidine-2,4-dione and 4'-bromomethyl-4-chlorobiphenyl in N,N-dimethylformamide. Trituration with diethyl ether provided an off-white solid. $^1$H NMR: δ 7.99 (s, 1H), 7.93 (dm, J=9.0 Hz, 2H), 7.45–7.49 (m, 4H), 7.38–7.41 (m, 2H), 7.23–7.26 (m, 2H), 7.06 (dm, J=9.0 Hz, 2H), 3.97, (A of AB, J=13.7 Hz, 1H), 3.92 (s, 3H), 3.39 (B of AB, J=13.7 Hz, 1H). MS (m/e): 486.0 & 488.0 (M−H)$^-$Cl isotopes. Anal: Calc for C$_{23}$H$_{18}$ClNO$_5$S$_2$.C$_3$H$_7$NO: 55.66% C, 4.49% H, 4.99% N; Found: 55.57% C, 4.41% H, 4.85% N. MP: 197–200° C.

EXAMPLE 22

5-(4-Methoxybenzenesulfonyl)-5-(3'-(trifluoromethyl)biphen-4-ylmethyl)thiazolidine-2,4-dione Prepared analogously to Example 9 from from 5-(4-methoxybenzenesulfonyl)thiazolidine-2,4-dione and 4'-bromomethyl-3-(trifluoromethyl)biphenyl in N,N-dimethylformamide. Column chromatography provided a light yellow glass. $^1$H NMR: δ 7.93 (dm, J=9.0 Hz, 2H), 7.78 (br s, 2H), 7.72 (d, J=7.5 Hz, 1H), 7.49–7.62 (m, 4H), 7.28 (dm, J=8.7 Hz, 2H), 7.07 (dm, J=9.0 Hz, 2H), 3.98 A of AB, J=13.7 Hz, 1H), 3.92 (s, 3H), 3.40 (B of AB, J=13.7 Hz, 1H). MS (m/e): 520.0 (M−H)$^-$. Anal: Calc for C$_{24}$H$_{18}$F$_3$NO$_5$S$_2$: 55.27% C, 3.48% H, 2.69% N; Found: 55.23% C, 3.70% H, 2.69% N.

EXAMPLE 23

5-(3',5'-Bis(trifluoromethyl)biphen-4-ylmethyl)-5-(4-methoxybenzenesulfonyl)thiazolidine-2,4-dione Prepared analogously to Example 9 from from 5-(4-methoxybenzenesulfonyl)thiazolidine-2,4-dione and 4'-bromomethyl-3,5-bis(trifluoromethyl)biphenyl in N,N-dimethylformamide. Trituration with diethyl ether provided a white solid. $^1$H NMR: δ 8.43 (br s, 1H), 7.91–7.99 (m, 4H), 7.85 (s, 1H), 7.53 (dd, J=6.5, 1.8 Hz, 2H), 7.33 (d, J=8.3 Hz, 2H), 7.07 (dm, J=9.0 Hz, 2H), 4.00 (A of AB, J=13.7 Hz, 1H), 3.93 (s, 3H), 3.42 (B of AB), J=13.7 Hz, 1H). MS (m/e): 588.5 (M−H)$^-$. Anal: Calc for C$_{25}$H$_{17}$F$_6$NO$_5$S$_2$.C$_3$H$_7$NO: 50.75% C, 3.65% H, 4.23% N; Found: 50.70% C, 3.60% H, 4.01% N. MP: 122–125° C.

EXAMPLE 24

5-(2',4'-Dichlorobiphen-4-ylmethyl)-5-(4-methoxybenzenesulfonyl)thiazolidine-2,4-dione Prepared analogously to Example 9 from from 5-(4-methoxybenzenesulfonyl)thiazolidine-2,4-dione and 4'-bromomethyl-2,4-dichlorobiphenyl in N,N-dimethylformamide. Column chromatography provided an off-white solid. $^1$H NMR: δ 8.01 (v br s, 1H), 7.93 (dm, J=9.0 Hz, 2H), 7.47 (d, J=2.0 Hz, 1H), 7.22–7.35 (m, 6H), 7.07 (dm, J=9.0 Hz, 2H), 3.98 (a of ab, J=13.7 Hz, 1H), 3.93 (s, 3H), 3.40 (b of ab, J=13.7 Hz, 1H). MS (m/e): 519.9 (M−H)$^-$. Anal: Calc for C$_{23}$H$_{17}$Cl$_2$NO$_5$S$_2$.0.75 C$_4$H$_{10}$O:

54.03% C, 4.27% H, 2.42% N; Found: 53.63% C, 4.33% H, 2.23% N. MP: 104–107° C.

EXAMPLE 25

5-[3-(3-Chlorophenoxy)benzyl]-5-(4-methylbenzenesulfanyl)thiazolidine-2,4-dione

Prepared analogously to Example 8 from 3-(bromomethyl)phenyl 4-chlophenyl ether. Column chromatography provided an amorphous solid. $^1$H NMR: δ 7.57 (br s, 1H), 7.46 (d, J=8.0 Hz, 2H), 7.27–7.30 (m, 3H), 7.17 (d, J=7.9 Hz, 2H), 7.02 (d, J=7.6 Hz, 1H), 6.88–6.95 (m, 4H), 3.64 (a of ab, J=13.9 Hz, 1H), 3.29 (b of ab, J=13.9 Hz, 1H), 2.36 (s, 3H). $^{13}$C NMR: δ 182.3, 173.3, 167.2, 156.9, 155.6, 141.6, 137.3, 135.7, 130.1, 130.0, 129.8, 128.5, 125.8, 124.6, 121.1, 120.1, 118.5, 72.5, 43.0, 21.4. MS (m/e): 453.9 (M–H)$^-$. Anal: Calc for $C_{23}H_{18}NO_3S_2 \cdot 0.5H_2O$: 59.41% C, 4.12% H, 3.01% N; Found: 59.73% C, 3.85% H, 2.82% N.

EXAMPLE 26

5-[3-(2-thiophen-2-yl[1,3]dioxolan-2-yl)benzyl]-5-(4-methylbenzenesulfonyl)thiazolidine-2,4-dione Prepared analogously to Example 9 from 2-[(3-bromomethyl)phenyl]-2-(2-thienyl)-1,3-dioxolane in N,N-dimethylformamide as the solvent. Column chromatography provided an amorphous solid. $^1$H NMR: δ 7.92 (br s, 1H), 7.85 (d, J=8.0 Hz, 2H), 7.52 (d, J=7.6 Hz, 1H), 7.38–7.40 (m, 3H), 7.25–7.30 (m, 2H), 7.13 (d, J=7.6 Hz, 1H), 6.88 (dd, J=4.8, 3.6 Hz, 1H), 6.76 (d, J=3.2 Hz, 1H), 4.12–4.18 (m, 2H), 3.93–3.99 (m, 2H), 3.91 (A of AB, J=13.6, 1H), 3.34 (B of AB, J=13.6, 1H), 2.48 (s, 3H). $^{13}$C NMR: δ 168.0, 166.1, 147.1, 146.0, 142.0, 131.7, 131.4, 130.8, 130.4, 129.9, 128.7, 128.7, 126.6, 126.4, 126.4, 126.0, 107.4, 85.9, 65.2, 36.8, 21.8. MS (m/e): 516.0 (M+H)$^+$. Anal: Calc for $C_{24}H_{21}NO_6S_3 \cdot H_2O$: 54.02% C, 4.34% H, 2.62% N; Found: 54.22% C, 4.34% H, 2.62% N.

EXAMPLE 27

2-[5-Benzyl-5-(4-methoxybenzenesulfonyl)2,4-dioxothiazolidin-3-yl]-acetic acid

To a solution of 5-Benzyl-5-(4-methoxybenzenesulfonyl)thiazolidine-2,4-dione (Example 6) (0.740 g, 1.96 mmol) in 34.5 mL of acetone was added t-butyl bromoacetate (4.227 g, 21.67 mmol) and potassium carbonate (2.75 g, 19.90 mmol) and the mixture was stirred for 16 h at room temperature under a nitrogen atmosphere. The mixture was filtered and concentrated in vacuo. Column chromatography provided the t-butyl ester of the title compound as a viscous yellow oil. This material was dissolved in 96 mL of dichloromethane and 17.8 mL of trifluroacetic acid was added and the mixture was stirred 2.5 h at room temperature under a nitrogen atmosphere. The mixture was concentrated in vacuo, triturated with hexane, and filtered. The solid was redissolved in dichloromethane and again concentrated in vacuo to give 0.720 g of the title compound as a beige solid.

MS (m/e): 436.0 (M+H)$^+$.

What is claimed is:

1. A compound of Formula (I) represented by the structure:

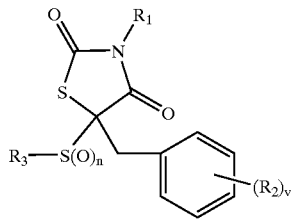

Formula (I)

wherein:

$R_1$ is hydrogen, $-CH_2-CO_2R_9$, or $-CH_2-C(O)NHOR_{10}$;

n is an integer of 0 or 2;

v is an integer of 1 to 3;

each $R_2$ is independently hydrogen, alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkyl(1 to 12 carbon atoms)amino, di(alkyl of 1 to 12 carbon atoms)amino, monoaryl(6 to 12 carbon atoms)amino, alkyl(1 to 12 carbon atoms)aryl(6 to 12 carbon atoms)amino, di(aryl of 6 to 12 carbon atoms) amino, monocycloalkyl(3 to 7 carbon atoms)amino, di(cycloalkyl of 3 to 7 carbon atoms)amino, alkyl(1 to 12 carbon atoms)cycloalkyl(3 to 7 carbon atoms) amino, aryl(6 to 12 carbon atoms)cycloalkyl(3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl(1 to 12 carbon atoms), carboxyaryl(6 to 12 carbon atoms), carboxycycloalkyl(3 to 7 carbon atoms), formyl, acyloxy of 1 to 12 carbon atoms, cyano, alkyl(1 to 12 carbon atoms)carbonyldioxy, aryl(6 to 12 carbon atoms)carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, monoalkyl(1 to 12 carbon atoms)carbamyl, di(alkyl of 1 to 12 carbon atoms) carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aminocarbonyloxy, aminocarbonylamino, or optionally when v is an integer of 1, the moiety

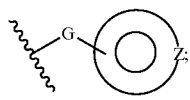

wherein the moiety

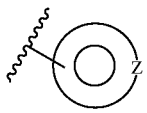

is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy and a moiety of the formula:

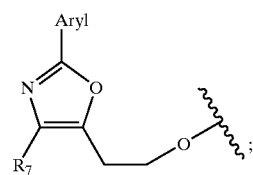

G is a single covalent bond, —O—, —S—, —SO—, —SO$_2$—, —N—R$_4$, —CH$_2$—, —CHOR$_4$, —CR$_8$OR$_4$, —C(OR$_5$)$_2$, —CO—, —CS—, —C=N—R$_6$ or moieties of the formulae:

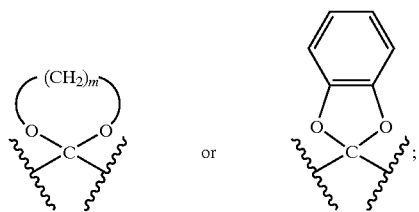

m is an integer of 2 to 4;

R$_3$ is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms)amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

or heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms)amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycloalkyl of 3 to 7 carbon atoms, formyl, acyloxy of 1 to 12 carbon atoms, cyano, alkyl(1 to 12 carbon atoms)carbonyldioxy, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

R$_4$ is hydrogen, alkyl of 1 to 12 carbon atoms, cycloalkyl of 3 to 7 carbon atoms, aryl of 6 to 12 carbon atoms optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms)amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

acyl of 1 to 12 carbon atoms, carboxyalkyl of 1 to 12 carbon atoms, carboxycycloalkyl of 3 to 7 carbon atoms, carboxyaryl of 6 to 12 carbon atoms wherein the aryl is optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms)amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms; formyl, carbamyl, monoalkyl(1 to 12 carbon atoms)carbamyl, di(alkyl of 1 to 12 carbon atoms)carbamyl, monoaryl(6 to 12 carbon atoms) carbamyl, di(aryl 6 to 12 carbon atoms)carbamyl, monocycloalkyl(3 to 7 carbon atoms)carbamyl, di(cycloalkyl 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl,-cycloalkyl(3 to 7 carbon atoms)aryl(6 to 12 carbon atoms)carbamyl, monoalkyl(1 to 12 carbon atoms)carboxyl, di(alkyl of 1 to 12 carbon atoms) carboxyl, monoaryl(6 to 12 carbon atoms)carboxyl, di(aryl 6 to 12 carbon atoms)carboxyl, monocycloalkyl(3 to 7 carbon atoms)carboxyl, di(cycloalkyl 3 to 7 carbon atoms)carboxyl, aryl(6 to 12 carbon atoms)alkyl(1 to 12 carbon atoms)carboxyl, cycloalkyl(3 to 7 carbon atoms)alkyl(1 to 12 carbon atoms)carboxyl, cycloalkyl(3 to 7 carbon atoms)aryl(6 to 12 carbon atoms) carboxylperfluoroaryl, monoalkyl(1 to 12 carbon atoms)thiocarbamyl, di(alkyl of 1 to 12 carbon atoms)thiocarbamyl, monoaryl(6 to 12 carbon atoms)thiocarbamyl, di(aryl 6 to 12 carbon atoms)thiocarbamyl, monocycloalkyl(3 to 7 carbon atoms)thiocarbamyl, di(cycloalkyl 3 to 7 carbon atoms) thiocarbamyl, aryl(6 to 12 carbon atoms)alkyl(1 to 12 carbon atoms)thiocarbamyl, cycloalkyl(3 to 7 carbon atoms)alkyl(1 to 12 carbon atoms) thiocarbamyl, or cycloalkyl(3 to 7 carbon atoms)aryl(6 to 12 carbon atoms)thiocarbamyl; heteroaryl of 5 to 12 ring atoms optionally substituted with 1 to 3 groups independently selected alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms)amino, (aryl of 6 to 12 carbon atoms)(cycloalkyl of 3 to 7 carbon atoms) amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_5$ is alkyl of 1 to 12 carbon atoms;

$R_6$ is alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, di(alkyl of 1 to 12 carbon atoms)amino, monoarylamino of 6 to 12 carbon atoms, alkyl(of 1 to 12 carbon atoms)aryl(of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, alkyl(of 1 to 12 carbon atoms)cycloalkyl (of 3 to 7 carbon atoms)amino, aryl(of 6 to 12 carbon atoms)cycloalkyl(of 3 to 7 carbon atoms)amino, arylsulfamoyl of 6 to 12 carbon atoms;

$R_7$ is alkyl of 1 to 12 carbon atoms;

$R_8$ is alkyl of 1 to 12 carbon atoms, cycloalkyl of 3 to 7 atoms and phenyl;

$R_9$ is hydrogen or alkyl of 1 to 6 carbon atoms;

$R_{10}$ is hydrogen or benzyl optionally substituted with nitro; and the pharmacologically acceptable salts thereof.

2. A compound according to claim 1 wherein $R_3$ is aryl; $R_1$ is H; and v is an integer of 1 or a pharmaceutically acceptable salt thereof.

3. A compound according to claim 1 wherein $R_3$ is aryl; $R_1$ is H; v is an integer of 1 and $R_2$ is a moiety

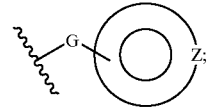

or a pharmaceutically acceptable salt thereof.

4. A compound according to claim 1 wherein $R_3$ is aryl; v is an integer of 1; $R_2$ is the moiety

the moiety

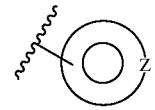

is heteroaryl optionally substituted with 1 to 3 groups independently selected or a pharmaceutically acceptable salt thereof.

5. A compound according to claim 1 wherein $R_3$ is aryl; v is an integer of 1; $R_2$ is the moiety

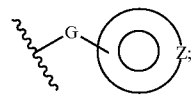

the moiety

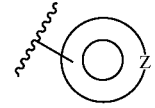

is aryl optionally substituted with 1 to 3 groups independently selected or a pharmaceutically acceptable salt thereof.

6. The compound of claim 1, wherein the compound is selected from the group consisting of 5-(4-[2-(5-Methyl-2-phenyloxazol-4-yl)ethoxy]benzyl)-5-(4-methylbenzenesulfonyl)thiazolidine-2,4-dione, 5-(4-Bromo-2-fluorobenzyl)-5-(4-methylbenzenesulfonyl)thiazolidine-2,4-dione, 5-(3,4-Dichlorobenzyl)-5-(4-methylbenzenesulfonyl)thiazolidine-2,4-dione, 5-(4-Bromo-2-fluorobenzyl)-5-(naphthalene-2-sulfonyl)thiazolidine-2,4-dione, 5-(4-[2-(5-Methyl-2-phenyloxazol-4-yl)ethoxy]benzyl)-5-(naphthalene-2-sulfonyl)thiazolidine-2,4-dione, 5-Benzyl-5-(4-methoxybenzenesulfonyl)thiazolidine-2,4-dione, 2-[5-Benzyl-5-(4-methoxybenzenesulfonyl)-2,4-dioxothiazolidin-3-yl]-N-hydroxyacetamide, 5-(3-[2-(4-Methoxyphenyl)[1,3]dioxolan-2-yl]benzyl)-5-(4-methylbenzenesulfanyl)thiazolidine-2,4-dione, 5-(3-[2-(4-Methoxyphenyl)[1,3]dioxolan-2-yl]benzyl)-5-(4-methylbenzenesulfonyl)thiazolidine-2,4-dione, 5-(3-(4-methoxybenzoyl)benzyl)-5-(4-methylbenzenesulfonyl)thiazolidine-2,4-dione, 5-(3-(4-methoxybenzoyl)benzyl)-5-(4-methylbenzenesulfanyl)thiazolidine-2,4-dione, 5-(3-[Hydroxy(4-methoxyphenyl)methyl]-benzyl)-5-(4-methylbenzenesulfanyl)thiazolidine-2,4-dione, 5-(4-Bromobenzyl-5-(4-methylbenzenesulfonyl)thiazolidine-2,4-dione, 5-[2'-cyanobiphen-4-yl methyl]-5-(4-methylbenzenesulfonyl)thiazolidine-2,4-dione, 5-[2'-(1H-Tetrazol-5-yl)biphen-4-ylmethyl]-5-(4-methylbenzenesulfonyl)thiazolidine-2,4-dione, 5-[2'-cyanobiphen-4-ylmethyl]-5-(4-methoxybenzenesulfonyl)thiazolidine-2,4-dione, 5-[3-(4-Methoxybenzyl)benzyl]-5-(4-methylbenzenesulfanyl)thiazolidine-2,4-dione, 5-[3-(2-Thiophen-2-yl[1,3]dioxolan-2-yl)benzyl]-5-(4-methylbenzenesulfanyl)thiazolidine-2,4-dione, 5-[3-(Thiophene-2-carbonyl)benzyl]-5-(4-methylbenzenesulfanyl)thiazolidine-2,4-dione, 5-Biphen-4-ylmethyl-5-(4-methoxybenzenesulfonyl)thiazolidine-2,4-dione, 5-(4'-Chlorobiphen-4-ylmethyl)-5-(4-methoxybenzenesulfonyl)thiazolidine-2,4-dione, 5-(4-Methoxybenzenesulfonyl)-5-(3'-(trifluoromethyl)biphen-4-ylmethyl)thiazolidine-2,4-dione, 5-(3',5'-Bis(trifluoromethyl)biphen-4-ylmethyl)-5-(4-methoxybenzenesulfonyl)thiazolidine-2,4-dione, 5-(2',4'-Dichlorobiphen-4-ylmethyl)-5-(4-methoxybenzenesulfonyl)thiazolidine-2,4-dione, 5-[3-(3-Chlorophenoxy)benzyl]-5-(4-methylbenzenesulfanyl)thiazolidine-2,4-dione, 5-[3-(2-thiophen-2-yl[1,3]dioxolan-2-yl)benzyl]-5-(4-methylbenzenesulfonyl)thiazolidine-2,4-dione, and 2-[5-Benzyl-5-(4-methoxybenzenesulfonyl)2,4-dioxothiazolidin-3-yl]-acetic acid or a pharmaceutically acceptable salt thereof.

7. A pharmaceutical composition comprising an effective amount of a compound of claim 1 in combination with one or more pharmaceutically acceptable carriers.

8. A pharmaceutical composition according to claim 7 wherein $R_3$ is aryl; $R_1$ is H; and v is an integer of 1 or a pharmaceutically acceptable salt thereof.

9. A pharmaceutical composition according to claim 7 wherein $R_3$ is aryl; $R_1$ is H; v is an integer of 1 and $R_2$ is a moiety

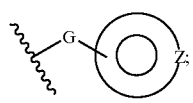

or a pharmaceutically acceptable salt thereof.

10. A pharmaceutical composition according to claim 7 wherein $R_3$ is aryl; v is an integer of 1; $R_2$ is the moiety

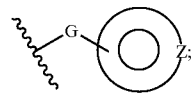

the moiety

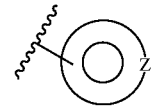

is heteroaryl optionally substituted with 1 to 3 groups independently selected or a pharmaceutically acceptable salt thereof.

11. A pharmaceutical composition according to claim 7 wherein $R_3$ is aryl; v is an integer of 1; $R_2$ is the moiety

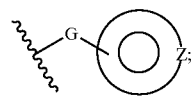

the moiety

is aryl optionally substituted with 1 to 3 groups independently selected or a pharmaceutically acceptable salt thereof.

12. A method of treating, inhibiting or controlling a ras-associated disease by inhibiting farnesyl-protein transferase(FPTase) enzyme in a mammal in need thereof, which comprises administering to said mammal an effective amount of a compound of Formula (I):

Formula (I)

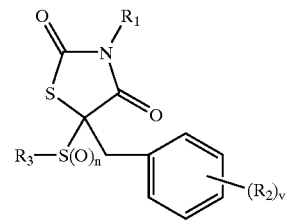

wherein:

$R_1$ is hydrogen, —$CH_2$—$CO_2R_9$, or —$CH_2$—C(O)NHOR$_{10}$;

n is an integer of 0 or 2;

v is an integer of 1 to 3;

each $R_2$ is independently hydrogen, alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkyl(1 to 12 carbon atoms)amino, di(alkyl of 1 to 12 carbon atoms)amino, monoaryl(6 to 12 carbon atoms)amino, alkyl(1 to 12 carbon atoms)aryl(6 to 12 carbon atoms)amino, di(aryl of 6 to 12 carbon atoms)

amino, monocycloalkyl(3 to 7 carbon atoms)amino, di(cycloalkyl of 3 to 7 carbon atoms)amino, alkyl(1 to 12 carbon atoms)cycloalkyl(3 to 7 carbon atoms) amino, aryl(6 to 12 carbon atoms)cycloalkyl(3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl(1 to 12 carbon atoms), carboxyaryl(6 to 12 carbon atoms), carboxycycloalkyl(3 to 7 carbon atoms), formyl, acyloxy of 1 to 12 carbon atoms, cyano, alkyl(1 to 12 carbon atoms)carbonyldioxy, aryl(6 to 12 carbon atoms)carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, monoalkyl(1 to 12 carbon atoms)carbamyl, di(alkyl of 1 to 12 carbon atoms) carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aminocarbonyloxy, aminocarbonylamino, or optionally when v is an integer of 1, the moiety

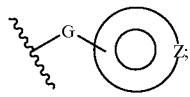

wherein the moiety

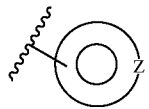

is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms)

carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy and a moiety of the formula:

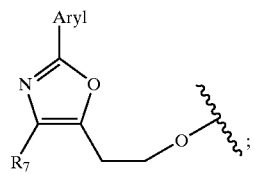

G is a single covalent bond, —O—, —S—, —SO—, —SO$_2$—, —N—R$_4$, —CH$_2$—, —CHOR$_4$—CR$_8$OR$_4$, —C(OR$_5$)$_2$, —CO—, —CS—, —C=N—R$_6$ or moieties of the formulae:

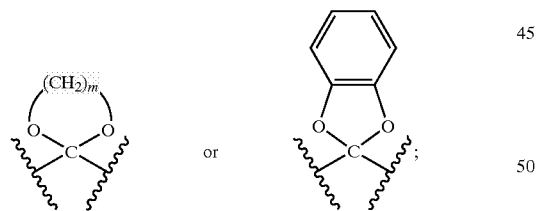

m is an integer of 2 to 4;

R$_3$ is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

or heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_4$ is hydrogen, alkyl of 1 to 12 carbon atoms, cycloalkyl of 3 to 7 carbon atoms, aryl of 6 to 12 carbon atoms optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

acyl of 1 to 12 carbon atoms, carboxyalkyl of 1 to 12 carbon atoms, carboxycycloalkyl of 3 to 7 carbon atoms, carboxyaryl of 6 to 12 carbon atoms wherein the aryl is optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms; formyl, carbamyl, monoalkyl(1 to 12 carbon atoms)carbamyl, di(alkyl of 1 to 12 carbon atoms)carbamyl, monoaryl(6 to 12 carbon atoms) carbamyl, di(aryl 6 to 12 carbon atoms)carbamyl, monocycloalkyl(3 to 7 carbon atoms)carbamyl, di(cycloalkyl 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, monoalkyl(1 to 12 carbon atoms)carboxyl, di(alkyl of 1 to 12 carbon atoms) carboxyl, monoaryl(6 to 12 carbon atoms)carboxyl, di(aryl 6 to 12 carbon atoms)carboxyl, monocycloalkyl(3 to 7 carbon atoms)carboxyl, di(cycloalkyl 3 to 7 carbon atoms)carboxyl, aryl(6 to 12 carbon atoms)alkyl(1 to 12 carbon atoms)carboxyl, cycloalkyl(3 to 7 carbon atoms)alkyl(1 to 12 carbon atoms)carboxyl, cycloalkyl(3 to 7 carbon atoms)aryl(6 to 12 carbon atoms) carboxylperfluoroaryl, monoalkyl(1 to 12 carbon atoms)thiocarbamyl, di(alkyl of 1 to 12 carbon atoms)thiocarbamyl, monoaryl(6 to 12 carbon atoms)thiocarbamyl, di(aryl 6 to 12 carbon atoms)thiocarbamyl, monocycloalkyl(3 to 7 carbon atoms)thiocarbamyl, di(cycloalkyl 3 to 7 carbon atoms) thiocarbamyl, aryl(6 to 12 carbon atoms)alkyl(1 to 12 carbon atoms)thiocarbamyl, cycloalkyl(3 to 7 carbon atoms)alkyl(1 to 12 carbon atoms) thiocarbamyl, or cycloalkyl(3 to 7 carbon atoms)aryl(6 to 12 carbon atoms)thiocarbamyl; heteroaryl of 5 to 12 ring atoms optionally substituted with 1 to 3 groups independently selected alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms) (cycloalkyl of 3 to 7 carbon atoms)amino, (aryl of 6 to 12 carbon atoms)(cycloalkyl of 3 to 7 carbon atoms) amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_5$ is alkyl of 1 to 12 carbon atoms;

$R_6$ is alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, di(alkyl of 1 to 12 carbon atoms)amino, monoarylamino of 6 to 12 carbon atoms, alkyl(of 1 to 12 carbon atoms)aryl(of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, alkyl(of 1 to 12 carbon atoms)cycloalkyl (of 3 to 7 carbon atoms)amino, aryl(of 6 to 12 carbon atoms)cycloalkyl(of 3 to 7 carbon atoms)amino, arylsulfamoyl of 6 to 12 carbon atoms;

$R_7$ is alkyl of 1 to 12 carbon atoms;

$R_8$ is alkyl of 1 to 12 carbon atoms, cycloalkyl of 3 to 7 atoms and phenyl;

$R_9$ is hydrogen or alkyl of 1 to 6 carbon atoms;

$R_{10}$ is hydrogen or benzyl optionally substituted with nitro; and the pharmacologically acceptable salts thereof.

13. The method according to claim 12 wherein $R_3$ is aryl; $R_1$ is H; and v is an integer of 1 or a pharmaceutically acceptable salt thereof.

14. The method according to claim 12 wherein $R_3$ is aryl; $R_1$ is H; v is an integer of 1 and $R_2$ is a moiety

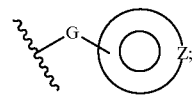

or a pharmaceutically acceptable salt thereof.

15. The method according to claim 12 wherein $R_3$ is aryl; v is an integer of 1; $R_2$ is the moiety

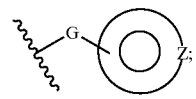

the moiety

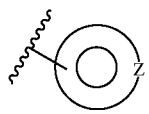

is heteroaryl optionally substituted with 1 to 3 groups independently selected or a pharmaceutically acceptable salt thereof.

16. The method according to claim 12 wherein $R_3$ is aryl; v is an integer of 1; $R_2$ is the moiety

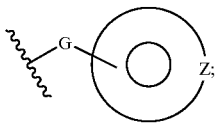

the moiety

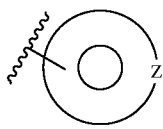

is aryl optionally substituted with 1 to 3 groups independently selected or a pharmaceutically acceptable salt thereof.

17. The method according to claim 12, wherein the compound is selected from the group consisting of 5-(4-[2-(5-Methyl-2-phenyloxazol-4-yl)ethoxy]benzyl)-5-(4-methylbenzenesulfonyl)thiazolidine-2,4-dione, 5-(4-Bromo-2-fluorobenzyl)-5-(4-methylbenzenesulfonyl)thiazolidine-2,4-dione, 5-(3,4-Dichlorobenzyl)-5-(4-methylbenzenesulfonyl)thiazolidine-2,4-dione, 5-(4-Bromo-2-fluorobenzyl)-5-(naphthalene-2-sulfonyl)thiazolidine-2,4-dione, 5-(4-[2-(5-Methyl-2-phenyloxazol-4-yl)ethoxy]benzyl)-5-(naphthalene-2-sulfonyl)thiazolidine-2,4-dione, 5-Benzyl-5-(4-methoxybenzenesulfonyl)thiazolidine-2,4-dione, 2-[5-Benzyl]-5-(4-methoxybenzenesulfonyl)-2,4-dioxothiazolidin-3-y 1N-hydroxyacetamide, 5-(3-[2-(4-Methoxyphenyl)[1,3]dioxolan-2-yl]benzyl)-5-(4-methylbenzenesulfanyl)thiazolidine-2,4-dione, 5-(3-[2-(4-Methoxyphenyl)[1,3]dioxolan-2-yl]benzyl)-5-(4-methylbenzenesulfonyl)thiazolidine-2,4-dione, 5-(3-(4-methoxybenzoyl)benzyl)-5-(4-methylbenzenesulfonyl)thiazolidine-2,4-dione, 5-(3-(4-methoxybenzoyl)benzyl)-5-(4-methylbenzenesulfanyl)thiazolidine-2,4-dione, 5-(3-[Hydroxy(4-methoxyphenyl)methyl]-benzyl)-5-(4-methylbenzenesulfanyl)thiazolidine-2,4-dione, 5-(4-Bromobenzyl-5-(4-methylbenzenesulfonyl)thiazolidine-2,4-dione, 5-[2'-cyanobiphen-4-ylmethyl]-5-(4-methylbenzenesulfonyl)thiazolidine-2,4-dione, 5-[2'-(1H-Tetrazol-5-yl)biphen-4-ylmethyl]-5-(4-methylbenzenesulfonyl)thiazolidine-2,4-dione, 5-[2'-cyanobiphen-4-ylmethyl]-5-(4-methoxybenzenesulfonyl)thiazolidine-2,4-dione, 5-[3-(4-Methoxybenzyl)benzyl]-5-(4-methylbenzenesulfanyl)thiazolidine-2,4-dione, 5-[3-(2-Thiophen-2-yl[1,3]dioxolan-2-yl)benzyl]-5-(4-methylbenzenesulfanyl)thiazolidine-2,4-dione, 5-[3-(Thiophene-2-carbonyl)benzyl]-5-(4-methylbenzenesulfanyl)thiazolidine-2,4-dione, 5-Biphen-4-ylmethyl-5-(4-methoxybenzenesulfonyl)thiazolidine-2,4-dione, 5-(4'-Chlorobiphen-4-ylmethyl)-5-(4-methoxybenzenesulfonyl)thiazolidine-2,4-dione, 5-(4-Methoxybenzenesulfonyl)-5-(3'-(trifluoromethyl)biphen-4-ylmethyl)thiazolidine-2,4-dione, 5-(3',5'-Bis(trifluoromethyl)biphen-4-ylmethyl)-5-(4-methoxybenzenesulfonyl)thiazolidine-2,4-dione, 5-(2',4'-Dichlorobiphen-4-ylmethyl)-5-(4-methoxybenzenesulfonyl)thiazolidine-2,4-dione, 5-[3-(3-Chlorophenoxy)benzyl]-5-(4-methylbenzenesulfanyl)thiazolidine-2,4-dione, 5-[3-(2-thiophen-2-yl[1,3]dioxolan-2-yl)benzyl]-5-(4-methylbenzenesulfonyl)thiazolidine-2,4-dione, and 2-[5-Benzyl-5-(4-methoxybenzenesulfonyl)2,4-dioxothiazolidin-3-yl]-acetic acid or a pharmaceutically acceptable salt thereof.

18. The method of claim 12 wherein the ras-associated disease in mammals is selected from the group consisting of cancers of the pancreas, breast, lung, colon, epidermis, prostate, bladder, thyroid, myelodysplastic tumors and myeloid leukemia.

19. The method of claim 12 wherein the ras-associated disease in mammals is selected from metastasis, suppressing angiogenesis, and inducing apoptosis.

20. The method of claim 12 wherein the ras-associated proliferative disease in mammals is restenosis, neurofibromatosis, endometriosis, and psoriasis.

21. The method of claim 12 wherein the ras-associated disease in mammals is prenyl modifications or proteins.

22. A process for the preparation of a compound of Formula (I):

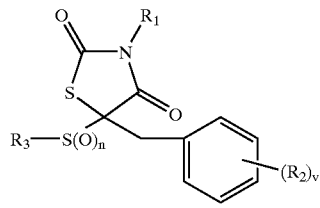

Formula (I)

wherein:

$R_1$ is hydrogen;

n is an integer of 0 or 2;

v is an integer of 1 to 3;

each $R_2$ is independently hydrogen, alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkyl(1 to 12 carbon atoms)amino, di(alkyl of 1 to 12 carbon atoms)amino, monoaryl(6 to 12 carbon atoms)amino, alkyl(1 to 12 carbon atoms)aryl(6 to 12 carbon atoms)amino, di(aryl of 6 to 12 carbon atoms) amino, monocycloalkyl(3 to 7 carbon atoms)amino, di(cycloalkyl of 3 to 7 carbon atoms)amino, alkyl(1 to 12 carbon atoms)cycloalkyl(3 to 7 carbon atoms)

amino, aryl(6 to 12 carbon atoms)cycloalkyl(3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl(1 to 12 carbon atoms), carboxyaryl(6 to 12 carbon atoms), carboxycycloalkyl(3 to 7 carbon atoms), formyl, acyloxy of 1 to 12 carbon atoms, cyano, alkyl(1 to 12 carbon atoms)carbonyldioxy, aryl(6 to 12 carbon atoms)carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aminocarbonyloxy, aminocarbonylamino, or optionally when v is an integer of 1, the moiety

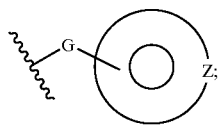

wherein the moiety

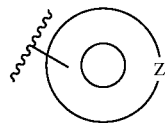

is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 —carbon atoms)(cycloalkyl of 3 to 7 carbon atoms)amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy and a moiety of the formula:

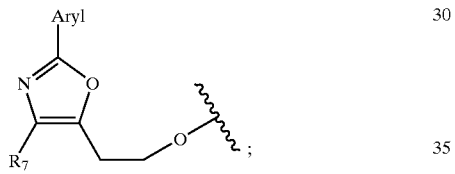

G is a single covalent bond, —O—, —S—, —SO—, —SO$_2$—, —N—R$_4$, —CH$_2$—, —CHOR$_4$—CR$_8$OR$_4$, —C(OR$_5$)$_2$, —CO—, —CS—, —C=N—R$_6$ or moieties of the formulae:

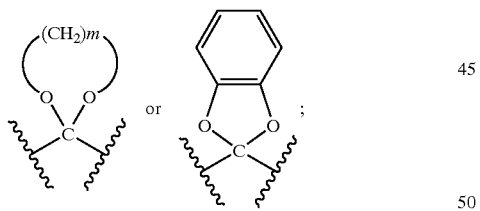

m is an integer of 2 to 4;

R$_3$ is aryl of 6 to 12 carbon atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

or heteroaryl of 5 to 12 ring atoms optionally substituted with 1 to 3 groups independently selected from alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_4$ is hydrogen, alkyl of 1 to 12 carbon atoms, cycloalkyl of 3 to 7 carbon atoms, aryl of 6 to 12 carbon atoms optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms;

acyl of 1 to 12 carbon atoms, carboxyalkyl of 1 to 12 carbon atoms, carboxycycloalkyl of 3 to 7 carbon atoms, carboxyaryl of 6 to 12 carbon atoms wherein the aryl is optionally substituted with 1 to 3 groups independently selected from substitutions include: alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms)(cycloalkyl of 3 to 7 carbon atoms) amino, (aryl of 6 to 12 carbon atoms)(cycloalkyl of 3 to 7 carbon atoms)amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, sulfo, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms)carbonyldioxy of 1 to 12 carbon atoms, aryl(6 to 12 carbon atoms)carbonyldioxy, cycloalkyl(3 to 7 carbon atoms)carbonyldioxy, carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms)acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms) sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms)sulfamyl, di(cycloalkyl of 3 to 7 carbon atoms)sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, aryloxy of 6 to 12 carbon atoms, perhaloaryl of 6 to 12 carbon atoms, cycloalkoxy of 3 to 7 carbon atoms; formyl, carbamyl, monoalkyl(1 to 12 carbon atoms)carbamyl, di(alkyl of 1 to 12 carbon atoms)carbamyl, monoaryl(6 to 12 carbon atoms) carbamyl, di(aryl 6 to 12 carbon atoms)carbamyl, monocycloalkyl(3 to 7 carbon atoms)carbamyl, di(cycloalkyl 3 to 7 carbon atoms)carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, monoalkyl(1 to 12 carbon atoms)carboxyl, di(alkyl of 1 to 12 carbon atoms) carboxyl, monoaryl(6 to 12 carbon atoms)carboxyl, di(aryl 6 to 12 carbon atoms)carboxyl, monocycloalkyl(3 to 7 carbon atoms)carboxyl, di(cycloalkyl 3 to 7 carbon atoms)carboxyl, aryl(6 to 12 carbon atoms)alkyl(1 to 12 carbon atoms)carboxyl, cycloalkyl(3 to 7 carbon atoms)alkyl(1 to 12 carbon atoms)carboxyl, cycloalkyl(3 to 7 carbon atoms)aryl(6 to 12 carbon atoms) carboxylperfluoroaryl, monoalkyl(1 to 12 carbon atoms)thiocarbamyl, di(alkyl of 1 to 12 carbon atoms)thiocarbamyl, monoaryl(6 to 12 carbon atoms)thiocarbamyl, di(aryl 6 to 12 carbon atoms)thiocarbamyl, monocycloalkyl(3 to 7 carbon atoms)thiocarbamyl, di(cycloalkyl 3 to 7 carbon atoms) thiocarbamyl, aryl(6 to 12 carbon atoms)alkyl(1 to 12 carbon atoms)thiocarbamyl, cycloalkyl(3 to 7 carbon atoms)alkyl(1 to 12 carbon atoms) thiocarbamyl, or cycloalkyl(3 to 7 carbon atoms)aryl(6 to 12 carbon atoms)thiocarbamyl; heteroaryl of 5 to 12 ring atoms optionally substituted with 1 to 3 groups independently selected alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, dialkylamino of 1 to 12 carbon atoms, monoarylamino of 6 to 12 carbon atoms, (alkyl of 1 to 12 carbon atoms)(aryl of 6 to 12 carbon atoms)amino, di(aryl of 6 to 12 carbon atoms)amino, monocycloalkylamino of 3 to 7 carbon atoms, di(cycloalkyl of 3 to 7 carbon atoms)amino, (alkyl of 1 to 12 carbon atoms) (cycloalkyl of 3 to 7 carbon atoms)amino, (aryl of 6 to 12 carbon atoms)(cycloalkyl of 3 to 7 carbon atoms) amino, mercapto, alkylthio of 1 to 12 carbon atoms, cycloalkylthio of 3 to 7 carbon atoms, arylthio of 6 to 12 carbon atoms, acyl of 1 to 12 carbon atoms, carboxyl, carboxyalkyl of 1 to 12 carbon atoms, carboxyaryl of 6 to 12 carbon atoms, carboxycycloalkyl of 3 to 7 carbon atoms, formyl, acyloxy of 1 to 12 carbon atoms, cyano, alkyl(1 to 12 carbon atoms) carbonyldioxy, aryl(6 to 12 carbon atoms) carbonyldioxy, cycloalkyl(3 to 7 carbon atoms) carbonyldioxy, carbamyl, acylamino of 1 to 12 carbon atoms, alkyl(1 to 12 carbon atoms)acylamino, cycloalkyl(3 to 7 carbon atoms)acylamino, aryl(6 to 12 carbon atoms)acylamino, nitro, perhaloalkyl of 1 to 12 carbon atoms, perhaloalkoxy of 1 to 12 carbon atoms, monoalkyl(1 to 12 carbon atoms)carbamyl, di(alkyl of 1 to 12 carbon atoms)carbamyl, monoaryl(6 to 12 carbon atoms)carbamyl, di(aryl of 6 to 12 carbon atoms)carbamyl, monocycloalkyl(3 to 7 carbon atoms) carbamyl, di(cycloalkyl of 3 to 7 carbon atoms) carbamyl, aryl(6 to 12 carbon atoms)alkyl(1 to 12 carbon atoms)carbamyl, cycloalkyl(3 to 7 carbon atoms)alkyl(1 to 12 carbon atoms)carbamyl, cycloalkyl(3 to 7 carbon atoms)aryl(6 to 12 carbon atoms)carbamyl, acylamino of 1 to 12 carbon atoms, alkyl(1 to 12 carbon atoms)acylamino of 1 to 12 carbon atoms, cycloalkyl(3 to 7 carbon atoms)acylamino of 1 to 12 carbon atoms, aryl(6 to 12 carbon atoms) acylamino of 1 to 12 carbon atoms, nitro, monoalkyl(1 to 12 carbon atoms)carbamyl, di(alkyl of 1 to 12 carbon atoms)carbamyl, monoaryl(6 to 12 carbon atoms) carbamyl, di(aryl of 6 to 12 carbon atoms)carbamyl, monocycloalkyl(3 to 7 carbon atoms)carbamyl, di(cycloalkyl of 3 to 7 carbon atoms)carbamyl, aryl(6 to 12 carbon atoms)alkyl(1 to 12 carbon atoms) carbamyl, cycloalkyl(3 to 7 carbon atoms)alkyl(1 to 12 carbon atoms)carbamyl, or cycloalkyl(3 to 7 carbon atoms)aryl(6 to 12 carbon atoms)carbamyl, monoalkyl(1 to 12 carbon atoms)sulfamyl, di(alkyl of 1 to 12 carbon atoms)sulfamyl, monoaryl(6 to 12 carbon atoms)sulfamyl, di(aryl of 6 to 12 carbon atoms)sulfamyl, monocycloalkyl(3 to 7 carbon atoms) sulfamyl, di(cycloalkyl of 3 to 7 carbon atoms) sulfamyl, aryl(6 to 12 carbon atoms)alkyl(1 to 12 carbon atoms)sulfamyl, cycloalkyl(3 to 7 carbon atoms)alkyl(1 to 12 carbon atoms)sulfamyl, or cycloalkyl(3 to 7 carbon atoms)aryl(6 to 12 carbon atoms)sulfamyl, perhaloaryl(6 to 12 carbon atoms), perhaloaryl(6 to 12 carbon atoms)oxy;

$R_5$ is alkyl of 1 to 12 carbon atoms;

$R_6$ is alkyl of 1 to 12 carbon atoms, cycloalkyl of 3 to 7 carbon atoms, aryl of 6 to 12 carbon atoms, alkoxy of 1 to 12 carbon atoms, cycloalkoxy of 3 to 7 carbon atoms, aryloxy of 6 to 12 carbon atoms, hydroxy, halo, amino, monoalkylamino of 1 to 12 carbon atoms, di(alkyl of 1 to 12 carbon atoms)amino, monoarylamino of 6 to 12 carbon atoms, alkyl(of 1 to 12 carbon atoms)aryl(of 6 to 12 carbon atoms)amino, di(aryl of 6 to 12 carbon atoms)amino, monocycloalkylamino of 3 to-7 carbon atoms, di(cycloalkyl of 3 to 7 carbon atoms)amino, alkyl(of 1 to 12 carbon atoms)cycloalkyl (of 3 to 7 carbon atoms)amino, aryl(of 6 to 12 carbon atoms)cycloalkyl(of 3 to 7 carbon atoms)amino, arylsulfamoyl of 6 to 12 carbon atoms;

$R_7$ is alkyl of 1 to 12 carbon atoms;

$R_8$ is alkyl of 1 to 12 carbon atoms, cycloalkyl of 3 to 7 atoms and phenyl; and the pharmacologically acceptable salts thereof, comprising:

a) reacting a compound of the formula

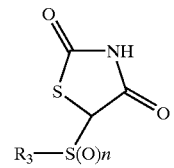

wherein $R_3$ and n are as defined above with a compound of formula

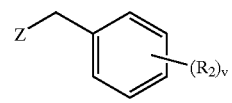

wherein $R_2$ and v are as defined above, and Z is a leaving group, preferably chloro, bromo, iodo, alkylsulfonyloxy of 1 to 10 carbon atoms, perfluoroalkylsulfonyloxy of 1 to 10 carbon atoms and phenylsulfonyloxy optionally substituted with from 1 to 3 substituents independently selected from halogen, alkyl of 1 to 10 carbon atoms, alkoxy of 1 to 10 carbon atoms, nitro and cyano in the presence of a base in an aprotic solvent to give a compound of Formula (I), and b) optionally converting a compound of formula (I) to a pharmaceutically acceptable salt.

23. The process according to claim 22 wherein the base is lithium hexamethyldisilylazide.

24. The process according to claim 22 wherein the aprotic solvent is N,N-dimethylformamide or tetrahydrofuran.

25. The process according to claim 22 further comprising oxidation when n is 0 with about a 2:1:1 mixture of potassium peroxymonosulfate, potassium hydrogen sulfate and potassium sulfate.

* * * * *

UNITED STATES PATENT AND TRADEMARK OFFICE
CERTIFICATE OF CORRECTION

PATENT NO. : 6,716,862 B2
DATED : April 6, 2004
INVENTOR(S) : Edward James Salaski, Semiramis Ayral-Kaloustian and Joseph William Epstein It is certified that error appears in the above-identified patent and that said Letters Patent is hereby corrected as shown below:

Column 51,
Lines 21-22, delete "5-[2'-(cyanobiphen-4-yl methyl]-5-(4-methylbenzenesulfonyl) thiazolidine-2,4-dione" and insert -- 5-[2'-(cyanobiphen-4-ylmethyl]-5-(4-methylbenzenesulfonyl)thiazolidine-2,4-dione --

Column 61,
Lines 46 and 47, "2-[5-Benzyl-5-(4-methoxybenzenesulfonyl)-2,4-dioxothiazolidin-3-y1N-hydroxyacetamide" and insert -- 2-[5-Benzyl-5-(4-methoxybenenesulfonyl)-2,4-dioxothiazolidin-3-yl]-N-hydroxyacetamide --

Signed and Sealed this

Fourteenth Day of December, 2004

JON W. DUDAS
*Director of the United States Patent and Trademark Office*